US009187737B2

(12) United States Patent
Breuer et al.

(10) Patent No.: US 9,187,737 B2
(45) Date of Patent: Nov. 17, 2015

(54) MUTANTS OF A PSEUDOMONAS GLUMAE BUTYNOL ESTERASE

(75) Inventors: Michael Breuer, Darmstadt (DE);
Bernhard Hauer, Fußgönheim (DE);
Ulrich Schwaneberg, Ritterhude (DE);
Tuck Seng Wong, Jiangsu (CN)

(73) Assignee: BASF SE, Ludwigshafen (DE)

( * ) Notice: Subject to any disclaimer, the term of this patent is extended or adjusted under 35 U.S.C. 154(b) by 731 days.

(21) Appl. No.: 12/306,703

(22) PCT Filed: Jun. 26, 2007

(86) PCT No.: PCT/EP2007/056367
§ 371 (c)(1),
(2), (4) Date: Dec. 2, 2009

(87) PCT Pub. No.: WO2008/000738
PCT Pub. Date: Jan. 3, 2008

(65) Prior Publication Data
US 2010/0068760 A1 Mar. 18, 2010

(30) Foreign Application Priority Data

Jun. 27, 2006 (EP) .................................. 06013236

(51) Int. Cl.
*C12P 7/62* (2006.01)
*C12N 9/18* (2006.01)
*C12N 9/16* (2006.01)
*C12P 41/00* (2006.01)

(52) U.S. Cl.
CPC ... *C12N 9/16* (2013.01); *C12P 7/62* (2013.01); *C12P 41/003* (2013.01)

(58) Field of Classification Search
CPC ....................................................... C12N 9/18
USPC ....................................................... 435/197
See application file for complete search history.

(56) References Cited

U.S. PATENT DOCUMENTS

| 6,596,520 | B1 | 7/2003 | Friedrich et al. | |
| 7,531,331 | B2 * | 5/2009 | Hauer et al. | 435/135 |
| 2005/0181472 | A1 | 8/2005 | Hauer et al. | |
| 2006/0286651 | A1 | 12/2006 | Kazlauskas et al. | |
| 2010/0196970 | A1 | 8/2010 | Hauer et al. | |
| 2010/0273223 | A1 | 10/2010 | Hauer et al. | |

FOREIGN PATENT DOCUMENTS

| EP | 0 892 044 A2 | 1/1999 |
| EP | 1069183 A2 | 1/2001 |
| WO | WO-02/18560 A2 | 3/2002 |
| WO | WO-2004/024954 A1 | 3/2004 |

OTHER PUBLICATIONS

GenBank Accession No. AF090329, GI:18860816, Aug. 2002, 4 pages.*
Poussu et al., Nucleic Acids Res. 33:e104, 2005, 8 pages.*
Faraldos, J., et al., "Biocatalysis in Organic Synthesis, 9. Highly Enantioselective Kinetic Resolution of Secondary Alcohols Catalyzed by Acylase", Synlett, 1997, vol. 4, pp. 367-370.
Khalameyzer, V., et al., "Screening, Nucleotide Sequence, and Biochemical Characterization of an Esterase from *Pseudomonas fluorescens* with High Activity towards Lactones", Applied and Environmental Microbiology, 1999, vol. 65, No. 2, pp. 477-482.
Manco, G., et al., "Overexpression and Properties of a New Thermophilic and Thermostable esterase from *Bacillus acidocaldarius* with Sequence Similarity to Hormone-Sensitive Lipase Subfamily", Biochem. J., 1998, vol. 332, pp. 203-212.
Peist, R., et al., "Characterization of the *aes* Gene of *Escherichia coli* Encoding an Enzyme with Esterase Activity", Journal of Bacteriology, 1997, vol. 179, No. 24, pp. 7679-7686.
Quyen, D. T., et al., "A Novel Esterase from *Ralstonia* sp. M1: Gene Cloning, Sequencing, High-Level Expression and Characterization", Protein Expression and Purification, 2007, vol. 51, pp. 133-140.
Yang, H., et al., "The Use of Vinyl Esters Significantly Enhanced Enantioselectivities and Reaction Rates in Lipase-Catalyzed Resolutions of Arylaliphatic Carboxylic Acids", Journal of Organic Chemistry, 1999, vol. 64, No. 5, pp. 1709-1712.
Balkenhohl, F., et al., "Optisch aktive Amine durch Lipase-katalysierte Methoxyacetylierung", Journal für praktische Chemie Chemiker-Zeitung, 1997, vol. 339, pp. 381-384 (Article in German, see English Language Abstract).
Gudelj, M., et al., "Novel *Rhodococcus* Esterases by Genetic Engineering", Journal of Molecular Catalysis B: Enzymatic, 1998, vol. 5, pp. 261-266.
Nakamura, K., et al., "Lipase-Catalyzed Kinetic Resolution of 3-Butyn-2-ol", Tetrahedron: Asymmetry, 1998, vol. 9, pp. 4429-4439.
"Hydrolase, alpha/beta fold family", NCBI Genbank Accession No. Q2T897, Oct. 31, 2006.
Itakura, K., et al., "Synthesis and Use of Synthetic Oligonucleotides", Ann. Rev. Biochem., 1984, vol. 53, pp. 323-356.
Kuchner, O., et al., "Directed Evolution of Enzyme Catalysts", TIBTECH, 1997, vol. 15, pp. 523-530.
Narang, S. A., et al., "DNA Synthesis", Tetrahedron, 1983, vol. 39, No. 1, pp. 3-22.
Pearson, W. R., et al., "Improved Tools for Biological Sequence Comparison", Proc. Natl. Acad. Sci. USA, 1988, vol. 85, pp. 2444-2448.
Reetz, M. T., et al., "Superior Biocatalysts by Directed Evolution", Topics in Current Chemistry, 1999, vol. 200, pp. 31-57.

(Continued)

Primary Examiner — David J Steadman
(74) Attorney, Agent, or Firm — Drinker Biddle & Reath LLP

(57) ABSTRACT

The invention relates to novel proteins having esterase activity, to mutants thereof, to nucleic acid sequences coding therefor, to expression cassettes, vectors and recombinant microorganisms; to methods for preparing said proteins and to the use thereof for enzymic, in particular enantioselective enzymic, ester hydrolysis or transesterification of organic esters.

14 Claims, 2 Drawing Sheets

(56) References Cited

OTHER PUBLICATIONS

Figure 3:
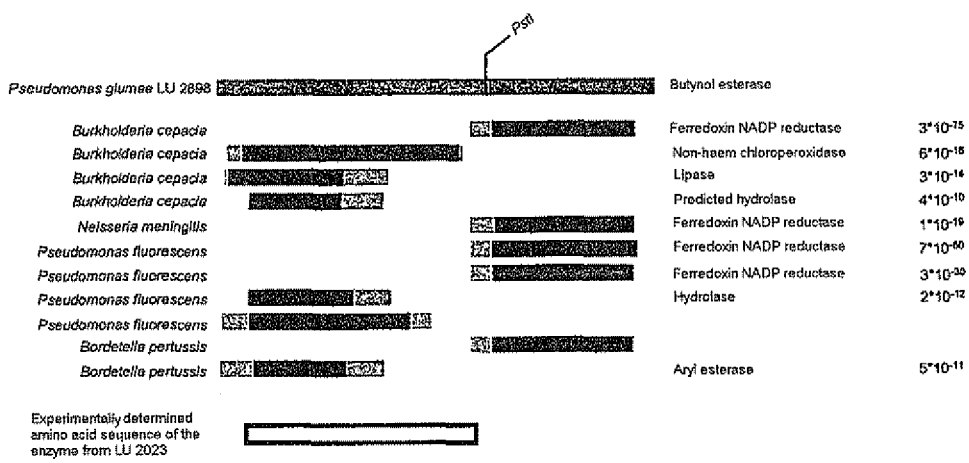

Zhao, H., et al., "Methods for Optimizing Industrial Enzymes by Directed Evolution", Chapter 49 in "Manual of Industrial Microbiology and Biotechnology", 1999, pp. 597-604.

Delagrave, S., et al., "Recursive Ensemble Mutagenesis", Protein Engineering, 1993, vol. 6, No. 3, pp. 327-331.

Arkin, A. P., et al., "An Algorithm for Protein Engineering: Simulations of Recursive Ensemble Mutagenesis", Proc. Natl. Acad. Sci. USA, 1992, vol. 89, pp. 7811-7815.

Ike, Y., et al., "Solid Phase Synthesis of Polynucleotides. VIII. Synthesis of Mixed Oligodeoxyribonucleotides by the Phosphotriester Solid Phase Method", Nucleic Acids Research, 1983, vol. 11, No. 2, pp. 477-488.

Itakura, K., et al., "Expression in *Escherichia coli* of a Chemically Synthesized Gene for the Hormone Somatostatin", Science, 1977, vol. 198, pp. 1056-1063.

Chica, R. A., et al., "Semi-Rational Approaches to Engineering Enzyme Activity: Combining the Benefits of Directed Evolution and Rational Design", Curr. Opin. Biotechnol., 2005, vol. 16, No. 4, pp. 378-384.

Seffernick, J. L., et al., "Melamine Deaminase and Atrazine Chlorohydrolase: 98 Percent Identical but Functionally Different", J. Bacteriol., 2001, vol. 183, No. 8, pp. 2405-2410.

Witkowski, A., et al., "Conversion of a β-Ketoacyl Synthase to a Malonyl Decarboxylase by Replacement of the Active-Site Cysteine with Glutamine", Biochemistry, 1999, vol. 38, pp. 11643-11650.

Butinol Esterase Mutant Experimental Data—"Expression of the Truncated 335 AA Butynol Esterase", Annex 1, 2006.

Butinol Esterase Mutant Experimental Data—"Expression of the Truncated 335 AA Butynol Esterase", Annex 2, 2006.

* cited by examiner

```
Query: 1420  IVVALYAVLFAFTLFTAHQVRRRFPPEGKFVEIDGDRLHYVDYGSGPPIVMVHGLCGQLL  1599
             ++V    V +  + +    ++     P  G+FVE+DG+R HY + G GPP+VM+HGL G
Sbjct:   11  VLVGASVVFWGLSAWMTRRIEAAVPGNGRFVEVDGERFHYYEEGKGPPLVMIHGLMGSSR  70

Query: 1600  NFAYLDLARLAQSHRVILVDRAGSGRSTRGPASRANVYAQARGIARFIETLGLERPVLVG  1779
             N  Y    +L +  RVI +DR GSG STR    + A++ AQAR +A FI  LGL++P+++G
Sbjct:   71  NLTYALSRQLREHFRVITLDRPGSGYSTRHKGTAADLPAQARQVAAFINQLGLDKPLVLG  130

Query: 1780  HSLGGAIALAVGLDYPERVSRIALIAPLTHTETEPPKXXXXXXXXXXXXXXXXXXXTMGIP  1959
             HSLGGAI+LA+ LD+PE VS +  L+APLTH +    P                 T+  +P
Sbjct:  131  HSLGGAISLALALDHPEAVSGLVLVAPLTHPQPRLPLVFWSLAVRPAWLRRFVANTLTVP  190

Query: 1960  IMILQSRKAIDAIFAPEPVPRDFPLKGGGMMGLRPEAFYAASSDLVAAPEDLPDMERRYP  2139
              + +L  R  +  +FAP+  P DF   +GGG++G+RP+  FYAASS++        + LP M +RYP
Sbjct:  191  MGLLTRRSVVKGVFAPDAAPEDFATRGGGLLGMRPDNFYAASSEIALVNDCLPGMVKRYP  250

Query: 2140  TLGVPVSMLYGRQDAILDFHKHGEGLKRKLDGVELSAVEG-GHMLPVT  2280
             L +P+ ++YG QD +LDF +HG+ L  K+ G++L  VEG GHMLP+T
Sbjct:  251  QLALPIGLIYGAQDKVLDFRRHGQALADKVPGLKLQVVEGRGHMLPIT  298
```

Fig. 1

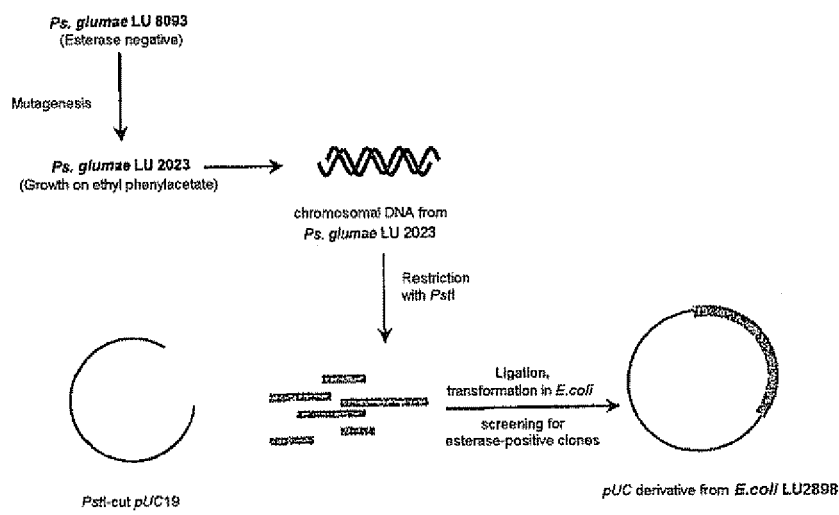

Fig. 2

SEQUENCE LISTING

<160> NUMBER OF SEQ ID NOS: 26

<210> SEQ ID NO 1
<211> LENGTH: 1530
<212> TYPE: DNA
<213> ORGANISM: Pseudomonas glumae
<220> FEATURE:
<221> NAME/KEY: CDS
<222> LOCATION: (1)..(1530)

<400> SEQUENCE: 1

```
atg atc gtc caa ctg atc gcc atc gtg gtc gcc ctc tac gcc gtg ctg      48
Met Ile Val Gln Leu Ile Ala Ile Val Val Ala Leu Tyr Ala Val Leu
1               5                   10                  15 ttc gcg ttc acg ctg ttc acc gcg cat cag gtg cgc cgc cgc ttt ccg      96
Phe Ala Phe Thr Leu Phe Thr Ala His Gln Val Arg Arg Arg Phe Pro
            20                  25                  30 ccc gag ggc aag ttc gtc gag atc gac ggc gac cgc ctg cat tat gtc     144
Pro Glu Gly Lys Phe Val Glu Ile Asp Gly Asp Arg Leu His Tyr Val
        35                  40                  45 gac tac ggc agc ggg ccg ccg atc gtg atg gtg cat ggc ctg tgc ggg     192
Asp Tyr Gly Ser Gly Pro Pro Ile Val Met Val His Gly Leu Cys Gly
    50                  55                  60 cag ctg ctg aac ttc gcc tac ctc gat ctg gcg cgg ctc gcg cag tcg     240
Gln Leu Leu Asn Phe Ala Tyr Leu Asp Leu Ala Arg Leu Ala Gln Ser
65                  70                  75                  80 cat cgc gtg atc ctc gtc gat cgg gcc ggc tcg gga cgc tcg acg cgc     288
His Arg Val Ile Leu Val Asp Arg Ala Gly Ser Gly Arg Ser Thr Arg
                85                  90                  95 ggc ccc gcc tcg cgc gcg aac gtc tat gcg cag gcg cgc ggc atc gcc     336
Gly Pro Ala Ser Arg Ala Asn Val Tyr Ala Gln Ala Arg Gly Ile Ala
            100                 105                 110 cgc ttc atc gag acg ctc ggc ctg gag cgg ccg gtg ctg gtg ggc cat     384
Arg Phe Ile Glu Thr Leu Gly Leu Glu Arg Pro Val Leu Val Gly His
        115                 120                 125 tcg ctc ggc ggc gcg atc gcg ctc gcg gtc ggc ctg gac tac ccc gag     432
Ser Leu Gly Gly Ala Ile Ala Leu Ala Val Gly Leu Asp Tyr Pro Glu
    130                 135                 140 cgc gtg agc cgc atc gcg ctg atc gcg ccg ctc acg cac acc gag acc     480
Arg Val Ser Arg Ile Ala Leu Ile Ala Pro Leu Thr His Thr Glu Thr
145                 150                 155                 160 gag ccg ccc aag gcg ttc cgc ggg ctc gcg ctg cgc ccg gcg gcg ctg     528
Glu Pro Pro Lys Ala Phe Arg Gly Leu Ala Leu Arg Pro Ala Ala Leu
                165                 170                 175
```

```
cgc cgc ttc gcg tcg ctg acg atg ggc atc ccg atc atg att ctg caa        576
Arg Arg Phe Ala Ser Leu Thr Met Gly Ile Pro Ile Met Ile Leu Gln
            180                 185                 190 agc cgc aag gcg atc gac gcg atc ttc gcg ccg gag ccg gtg ccg cgc        624
Ser Arg Lys Ala Ile Asp Ala Ile Phe Ala Pro Glu Pro Val Pro Arg
        195                 200                 205 gat ttc ccg ctg aag ggc ggc ggc atg atg ggg ctg cgg ccc gag gcg        672
Asp Phe Pro Leu Lys Gly Gly Gly Met Met Gly Leu Arg Pro Glu Ala
    210                 215                 220 ttc tac gcg gcg tcg tcg gac ctg gtc gcc gcg ccc gag gac ctg ccc        720
Phe Tyr Ala Ala Ser Ser Asp Leu Val Ala Ala Pro Glu Asp Leu Pro
225                 230                 235                 240 gac atg gag cgc cgc tac ccg acg ctg ggc gtg ccg gtc agc atg ctg        768
Asp Met Glu Arg Arg Tyr Pro Thr Leu Gly Val Pro Val Ser Met Leu
                245                 250                 255 tac ggg cgc cag gac gcg atc ctc gat ttc cac aag cat ggc gag ggg        816
Tyr Gly Arg Gln Asp Ala Ile Leu Asp Phe His Lys His Gly Glu Gly
            260                 265                 270 ctc aag cgc aag ctc gac ggc gtc gag ctg agc gcc gtc gag ggc ggg        864
Leu Lys Arg Lys Leu Asp Gly Val Glu Leu Ser Ala Val Glu Gly Gly
        275                 280                 285 cac atg ctg ccc gtg acg cag ccg gcc gcc acc acc gac tgg ctc ctc        912
His Met Leu Pro Val Thr Gln Pro Ala Ala Thr Thr Asp Trp Leu Leu
    290                 295                 300 gcg gtg gcc gcg gcg gcg aac gcg gcg gcg cag cac gat gcg gcg cgg        960
Ala Val Ala Ala Ala Ala Asn Ala Ala Ala Gln His Asp Ala Ala Arg
305                 310                 315                 320 ccg gat ccg gca ccg tcc gag gtc acg cag gcc ggc gcg ctg cag cat       1008
Pro Asp Pro Ala Pro Ser Glu Val Thr Gln Ala Gly Ala Leu Gln His
                325                 330                 335 ctg aag gtc ggc gac aac gtg ctg atc ggc aag aag ccc acc ggc acg       1056
Leu Lys Val Gly Asp Asn Val Leu Ile Gly Lys Lys Pro Thr Gly Thr
            340                 345                 350 ctg gtg gcc gac aac ctg ctg ccg ggc aag acc ctg tgg ctg ctg tcg       1104
Leu Val Ala Asp Asn Leu Leu Pro Gly Lys Thr Leu Trp Leu Leu Ser
        355                 360                 365 acc ggc acg ggt ctc gcg ccg ttc atg tcg atc atc cgc gat ccg gac       1152
Thr Gly Thr Gly Leu Ala Pro Phe Met Ser Ile Ile Arg Asp Pro Asp
    370                 375                 380 atc tac gaa cgc tac gag aag gtg gtc ctc acg cac acc tgc cgc ctg       1200
Ile Tyr Glu Arg Tyr Glu Lys Val Val Leu Thr His Thr Cys Arg Leu
385                 390                 395                 400 aag ggc gag ctc gcg tac atg gac ttc atc aag cac gac ctg ccg ggc       1248
Lys Gly Glu Leu Ala Tyr Met Asp Phe Ile Lys His Asp Leu Pro Gly
                405                 410                 415 cat gag tac ctc ggc gac atc atc aag gaa aag ctg atc tac tac ccg       1296
His Glu Tyr Leu Gly Asp Ile Ile Lys Glu Lys Leu Ile Tyr Tyr Pro
            420                 425                 430 acc gtc acg cgc gaa gcg ttc gac aac gag ggg cgg atc acc gac ctg       1344
Thr Val Thr Arg Glu Ala Phe Asp Asn Glu Gly Arg Ile Thr Asp Leu
        435                 440                 445 atc tcg acg ggc aag ctg ttc acc gat ctc gac gtc ccg ccg ttc tcg       1392
Ile Ser Thr Gly Lys Leu Phe Thr Asp Leu Asp Val Pro Pro Phe Ser
    450                 455                 460 ccc gag aac gac cgc gtg atg ctg tgc ggc agc acc gcg atg ctg aag       1440
Pro Glu Asn Asp Arg Val Met Leu Cys Gly Ser Thr Ala Met Leu Lys
465                 470                 475                 480 gac acc acc gac ctg ctc aag cag gcc ggc ctc gtc gaa ggc aag aac       1488
Asp Thr Thr Asp Leu Leu Lys Gln Ala Gly Leu Val Glu Gly Lys Asn
                485                 490                 495
```

```
agc gcg ccg ggc cac tat gtg atc gaa cgc gca ttt gtc gac         1530
Ser Ala Pro Gly His Tyr Val Ile Glu Arg Ala Phe Val Asp
            500                 505                 510

<210> SEQ ID NO 2
<211> LENGTH: 510
<212> TYPE: PRT
<213> ORGANISM: Pseudomonas glumae

<400> SEQUENCE: 2

Met Ile Val Gln Leu Ile Ala Ile Val Ala Leu Tyr Ala Val Leu
1               5                   10                  15

Phe Ala Phe Thr Leu Phe Thr Ala His Gln Val Arg Arg Phe Pro
                20                  25                  30

Pro Glu Gly Lys Phe Val Glu Ile Asp Gly Asp Arg Leu His Tyr Val
            35                  40                  45

Asp Tyr Gly Ser Gly Pro Pro Ile Val Met Val His Gly Leu Cys Gly
        50                  55                  60

Gln Leu Leu Asn Phe Ala Tyr Leu Asp Leu Ala Arg Leu Ala Gln Ser
65                  70                  75                  80

His Arg Val Ile Leu Val Asp Arg Ala Gly Ser Gly Arg Ser Thr Arg
                85                  90                  95

Gly Pro Ala Ser Arg Ala Asn Val Tyr Ala Gln Ala Arg Gly Ile Ala
            100                 105                 110

Arg Phe Ile Glu Thr Leu Gly Leu Glu Arg Pro Val Leu Val Gly His
        115                 120                 125

Ser Leu Gly Gly Ala Ile Ala Leu Ala Val Gly Leu Asp Tyr Pro Glu
    130                 135                 140

Arg Val Ser Arg Ile Ala Leu Ile Ala Pro Leu Thr His Thr Glu Thr
145                 150                 155                 160

Glu Pro Pro Lys Ala Phe Arg Gly Leu Ala Leu Arg Pro Ala Ala Leu
                165                 170                 175

Arg Arg Phe Ala Ser Leu Thr Met Gly Ile Pro Ile Met Ile Leu Gln
            180                 185                 190

Ser Arg Lys Ala Ile Asp Ala Ile Phe Ala Pro Glu Pro Val Pro Arg
        195                 200                 205

Asp Phe Pro Leu Lys Gly Gly Gly Met Met Gly Leu Arg Pro Glu Ala
    210                 215                 220

Phe Tyr Ala Ala Ser Ser Asp Leu Val Ala Ala Pro Glu Asp Leu Pro
225                 230                 235                 240

Asp Met Glu Arg Arg Tyr Pro Thr Leu Gly Val Pro Val Ser Met Leu
                245                 250                 255

Tyr Gly Arg Gln Asp Ala Ile Leu Asp Phe His Lys His Gly Glu Gly
            260                 265                 270

Leu Lys Arg Lys Leu Asp Gly Val Glu Leu Ser Ala Val Glu Gly Gly
        275                 280                 285

His Met Leu Pro Val Thr Gln Pro Ala Ala Thr Thr Asp Trp Leu Leu
    290                 295                 300

Ala Val Ala Ala Ala Asn Ala Ala Gln His Asp Ala Ala Arg
305                 310                 315                 320

Pro Asp Pro Ala Pro Ser Glu Val Thr Gln Ala Gly Ala Leu Gln His
                325                 330                 335

Leu Lys Val Gly Asp Asn Val Leu Ile Gly Lys Lys Pro Thr Gly Thr
            340                 345                 350
```

-continued

```
Leu Val Ala Asp Asn Leu Leu Pro Gly Lys Thr Leu Trp Leu Leu Ser
            355                 360                 365

Thr Gly Thr Gly Leu Ala Pro Phe Met Ser Ile Ile Arg Asp Pro Asp
        370                 375                 380

Ile Tyr Glu Arg Tyr Glu Lys Val Val Leu Thr His Thr Cys Arg Leu
385                 390                 395                 400

Lys Gly Glu Leu Ala Tyr Met Asp Phe Ile Lys His Asp Leu Pro Gly
                405                 410                 415

His Glu Tyr Leu Gly Asp Ile Ile Lys Glu Lys Leu Ile Tyr Tyr Pro
            420                 425                 430

Thr Val Thr Arg Glu Ala Phe Asp Asn Glu Gly Arg Ile Thr Asp Leu
        435                 440                 445

Ile Ser Thr Gly Lys Leu Phe Thr Asp Leu Asp Val Pro Pro Phe Ser
    450                 455                 460

Pro Glu Asn Asp Arg Val Met Leu Cys Gly Ser Thr Ala Met Leu Lys
465                 470                 475                 480

Asp Thr Asp Leu Leu Lys Gln Ala Gly Leu Val Glu Gly Lys Asn
                485                 490                 495

Ser Ala Pro Gly His Tyr Val Ile Glu Arg Ala Phe Val Asp
            500                 505                 510

<210> SEQ ID NO 3
<211> LENGTH: 32
<212> TYPE: PRT
<213> ORGANISM: Artificial sequence
<220> FEATURE:
<223> OTHER INFORMATION: Partial Sequence

<400> SEQUENCE: 3

Phe Ile Glu Thr Leu Gly Leu Glu Arg Pro Val Leu Val Gly His Ser
1               5                   10                  15

Leu Gly Gly Ala Ile Ala Leu Ala Val Gly Leu Asp Tyr Pro Glu Arg
                20                  25                  30

<210> SEQ ID NO 4
<211> LENGTH: 14
<212> TYPE: PRT
<213> ORGANISM: Artificial sequence
<220> FEATURE:
<223> OTHER INFORMATION: Partial Sequence

<400> SEQUENCE: 4

Ile Ala Leu Ile Ala Pro Leu Thr His Thr Glu Thr Glu Pro
1               5                   10

<210> SEQ ID NO 5
<211> LENGTH: 20
<212> TYPE: PRT
<213> ORGANISM: Artificial sequence
<220> FEATURE:
<223> OTHER INFORMATION: Partial Sequeence

<400> SEQUENCE: 5

Gly Gly Gly Met Met Gly Leu Arg Pro Glu Ala Phe Tyr Ala Ala Ser
1               5                   10                  15

Ser Asp Leu Val
            20

<210> SEQ ID NO 6
<211> LENGTH: 11
<212> TYPE: PRT
```

<210> SEQ ID NO 7
<211> LENGTH: 1005
<212> TYPE: DNA
<213> ORGANISM: Pseudomonas glumae
<220> FEATURE:
<221> NAME/KEY: CDS
<222> LOCATION: (1)..(1005)

<400> SEQUENCE: 7

| | | | | | | | | | | | | | | | | |
|---|---|---|---|---|---|---|---|---|---|---|---|---|---|---|---|---|
| atg | atc | gtc | caa | ctg | atc | gcc | atc | gtg | gtc | gcc | ctc | tac | gcc | gtg | ctg | 48 |
| Met | Ile | Val | Gln | Leu | Ile | Ala | Ile | Val | Val | Ala | Leu | Tyr | Ala | Val | Leu | |
| 1 | | | | 5 | | | | | 10 | | | | | 15 | | |
| ttc | gcg | ttc | acg | ctg | ttc | acc | gcg | cat | cag | gtg | cgc | cgc | cgc | ttt | ccg | 96 |
| Phe | Ala | Phe | Thr | Leu | Phe | Thr | Ala | His | Gln | Val | Arg | Arg | Arg | Phe | Pro | |
| | | | 20 | | | | | 25 | | | | | 30 | | | |
| ccc | gag | ggc | aag | ttc | gtc | gag | atc | gac | ggc | gac | cgc | ctg | cat | tat | gtc | 144 |
| Pro | Glu | Gly | Lys | Phe | Val | Glu | Ile | Asp | Gly | Asp | Arg | Leu | His | Tyr | Val | |
| | | 35 | | | | | 40 | | | | | 45 | | | | |
| gac | tac | ggc | agc | ggg | ccg | ccg | atc | gtg | atg | gtg | cat | ggc | ctg | tgc | ggg | 192 |
| Asp | Tyr | Gly | Ser | Gly | Pro | Pro | Ile | Val | Met | Val | His | Gly | Leu | Cys | Gly | |
| | 50 | | | | | 55 | | | | | 60 | | | | | |
| cag | ctg | ctg | aac | ttc | gcc | tac | ctc | gat | ctg | gcg | cgg | ctc | gcg | cag | tcg | 240 |
| Gln | Leu | Leu | Asn | Phe | Ala | Tyr | Leu | Asp | Leu | Ala | Arg | Leu | Ala | Gln | Ser | |
| 65 | | | | | 70 | | | | | 75 | | | | | 80 | |
| cat | cgc | gtg | atc | ctc | gtc | gat | cgg | gcc | ggc | tcg | gga | cgc | tcg | acg | cgc | 288 |
| His | Arg | Val | Ile | Leu | Val | Asp | Arg | Ala | Gly | Ser | Gly | Arg | Ser | Thr | Arg | |
| | | | | 85 | | | | | 90 | | | | | 95 | | |
| ggc | ccc | gcc | tcg | cgc | gcg | aac | gtc | tat | gcg | cag | gcg | cgc | ggc | atc | gcc | 336 |
| Gly | Pro | Ala | Ser | Arg | Ala | Asn | Val | Tyr | Ala | Gln | Ala | Arg | Gly | Ile | Ala | |
| | | | 100 | | | | | 105 | | | | | 110 | | | |
| cgc | ttc | atc | gag | acg | ctc | ggc | ctg | gag | cgg | ccg | gtg | ctg | gtg | ggc | cat | 384 |
| Arg | Phe | Ile | Glu | Thr | Leu | Gly | Leu | Glu | Arg | Pro | Val | Leu | Val | Gly | His | |
| | | 115 | | | | | 120 | | | | | 125 | | | | |
| tcg | ctc | ggc | ggc | gcg | atc | gcg | ctc | gcg | gtc | ggc | ctg | gac | tac | ccc | gag | 432 |
| Ser | Leu | Gly | Gly | Ala | Ile | Ala | Leu | Ala | Val | Gly | Leu | Asp | Tyr | Pro | Glu | |
| | 130 | | | | | 135 | | | | | 140 | | | | | |
| cgc | gtg | agc | cgc | atc | gcg | ctg | atc | gcg | ccg | ctc | acg | cac | acc | gag | acc | 480 |
| Arg | Val | Ser | Arg | Ile | Ala | Leu | Ile | Ala | Pro | Leu | Thr | His | Thr | Glu | Thr | |
| 145 | | | | | 150 | | | | | 155 | | | | | 160 | |
| gag | ccg | ccc | aag | gcg | ttc | cgc | ggg | ctc | gcg | ctg | cgc | ccg | gcg | gcg | ctg | 528 |
| Glu | Pro | Pro | Lys | Ala | Phe | Arg | Gly | Leu | Ala | Leu | Arg | Pro | Ala | Ala | Leu | |
| | | | | 165 | | | | | 170 | | | | | 175 | | |
| cgc | cgc | ttc | gcg | tcg | ctg | acg | atg | ggc | atc | ccg | atc | atg | att | ctg | caa | 576 |
| Arg | Arg | Phe | Ala | Ser | Leu | Thr | Met | Gly | Ile | Pro | Ile | Met | Ile | Leu | Gln | |
| | | | 180 | | | | | 185 | | | | | 190 | | | |
| agc | cgc | aag | gcg | atc | gac | gcg | atc | ttc | gcg | ccg | gag | ccg | gtg | ccg | cgc | 624 |
| Ser | Arg | Lys | Ala | Ile | Asp | Ala | Ile | Phe | Ala | Pro | Glu | Pro | Val | Pro | Arg | |
| | | 195 | | | | | 200 | | | | | 205 | | | | |
| gat | ttc | ccg | ctg | aag | ggc | ggc | ggc | atg | atg | ggg | ctg | cgg | ccc | gag | gcg | 672 |
| Asp | Phe | Pro | Leu | Lys | Gly | Gly | Gly | Met | Met | Gly | Leu | Arg | Pro | Glu | Ala | |
| | 210 | | | | | 215 | | | | | 220 | | | | | |
| ttc | tac | gcg | gcg | tcg | tcg | gac | ctg | gtc | gcc | gcg | ccc | gag | gac | ctg | ccc | 720 |
| Phe | Tyr | Ala | Ala | Ser | Ser | Asp | Leu | Val | Ala | Ala | Pro | Glu | Asp | Leu | Pro | |
| 225 | | | | | 230 | | | | | 235 | | | | | 240 | |

```
gac atg gag cgc cgc tac ccg acg ctg ggc gtg ccg gtc agc atg ctg      768
Asp Met Glu Arg Arg Tyr Pro Thr Leu Gly Val Pro Val Ser Met Leu
            245                 250                 255 tac ggg cgc cag gac gcg atc ctc gat ttc cac aag cat ggc gag ggg      816
Tyr Gly Arg Gln Asp Ala Ile Leu Asp Phe His Lys His Gly Glu Gly
            260                 265                 270 ctc aag cgc aag ctc gac ggc gtc gag ctg agc gcc gtc gag ggc ggg      864
Leu Lys Arg Lys Leu Asp Gly Val Glu Leu Ser Ala Val Glu Gly Gly
            275                 280                 285 cac atg ctg ccc gtg acg cag ccg gcc gcc acc acc gac tgg ctc ctc      912
His Met Leu Pro Val Thr Gln Pro Ala Ala Thr Thr Asp Trp Leu Leu
            290                 295                 300 gcg gtg gcc gcg gcg gcg aac gcg gcg gcg cag cac gat gcg gcg cgg      960
Ala Val Ala Ala Ala Ala Asn Ala Ala Ala Gln His Asp Ala Ala Arg
305                 310                 315                 320 ccg gat ccg gca ccg tcc gag gtc acg cag gcc ggc gcg ctg cag          1005
Pro Asp Pro Ala Pro Ser Glu Val Thr Gln Ala Gly Ala Leu Gln
                325                 330                 335

<210> SEQ ID NO 8
<211> LENGTH: 335
<212> TYPE: PRT
<213> ORGANISM: Pseudomonas glumae

<400> SEQUENCE: 8

Met Ile Val Gln Leu Ile Ala Ile Val Ala Leu Tyr Ala Val Leu
1               5                   10                  15

Phe Ala Phe Thr Leu Phe Thr Ala His Gln Val Arg Arg Phe Pro
                20                  25                  30

Pro Glu Gly Lys Phe Val Glu Ile Asp Gly Asp Arg Leu His Tyr Val
            35                  40                  45

Asp Tyr Gly Ser Gly Pro Pro Ile Val Met Val His Gly Leu Cys Gly
        50                  55                  60

Gln Leu Leu Asn Phe Ala Tyr Leu Asp Leu Ala Arg Leu Ala Gln Ser
65                  70                  75                  80

His Arg Val Ile Leu Val Asp Arg Ala Gly Ser Gly Arg Ser Thr Arg
                85                  90                  95

Gly Pro Ala Ser Arg Ala Asn Val Tyr Ala Gln Ala Arg Gly Ile Ala
            100                 105                 110

Arg Phe Ile Glu Thr Leu Gly Leu Glu Arg Pro Val Leu Val Gly His
            115                 120                 125

Ser Leu Gly Gly Ala Ile Ala Leu Ala Val Gly Leu Asp Tyr Pro Glu
        130                 135                 140

Arg Val Ser Arg Ile Ala Leu Ile Ala Pro Leu Thr His Thr Glu Thr
145                 150                 155                 160

Glu Pro Pro Lys Ala Phe Arg Gly Leu Ala Leu Arg Pro Ala Ala Leu
                165                 170                 175

Arg Arg Phe Ala Ser Leu Thr Met Gly Ile Pro Ile Met Ile Leu Gln
            180                 185                 190

Ser Arg Lys Ala Ile Asp Ala Ile Phe Ala Pro Glu Pro Val Pro Arg
            195                 200                 205

Asp Phe Pro Leu Lys Gly Gly Met Met Gly Leu Arg Pro Glu Ala
        210                 215                 220

Phe Tyr Ala Ala Ser Ser Asp Leu Val Ala Ala Pro Glu Asp Leu Pro
225                 230                 235                 240

Asp Met Glu Arg Arg Tyr Pro Thr Leu Gly Val Pro Val Ser Met Leu
```

```
                    245                 250                 255
Tyr Gly Arg Gln Asp Ala Ile Leu Asp Phe His Lys His Gly Glu Gly
            260                 265                 270

Leu Lys Arg Lys Leu Asp Gly Val Glu Leu Ser Ala Val Glu Gly Gly
        275                 280                 285

His Met Leu Pro Val Thr Gln Pro Ala Ala Thr Thr Asp Trp Leu Leu
    290                 295                 300

Ala Val Ala Ala Ala Asn Ala Ala Gln His Asp Ala Ala Arg
305                 310                 315                 320

Pro Asp Pro Ala Pro Ser Glu Val Thr Gln Ala Gly Ala Leu Gln
                325                 330                 335

<210> SEQ ID NO 9
<211> LENGTH: 24
<212> TYPE: DNA
<213> ORGANISM: Artificial sequence
<220> FEATURE:
<223> OTHER INFORMATION: PCR Primer

<400> SEQUENCE: 9
tttttgccct cgttatctag attt                                              24

<210> SEQ ID NO 10
<211> LENGTH: 33
<212> TYPE: DNA
<213> ORGANISM: Artificial sequence
<220> FEATURE:
<223> OTHER INFORMATION: PCR Primer

<400> SEQUENCE: 10
ccggaattcc ggtatctaac taagcttgac ctg                                    33

<210> SEQ ID NO 11
<211> LENGTH: 23
<212> TYPE: DNA
<213> ORGANISM: Artificial sequence
<220> FEATURE:
<223> OTHER INFORMATION: PCR Primer

<400> SEQUENCE: 11
gaccatgatt acgccaagct tgc                                               23

<210> SEQ ID NO 12
<211> LENGTH: 33
<212> TYPE: DNA
<213> ORGANISM: Artificial sequence
<220> FEATURE:
<223> OTHER INFORMATION: PCR Primer

<400> SEQUENCE: 12
ccggaattcc ggtcactgca gcgcgccggc ctg                                    33

<210> SEQ ID NO 13
<211> LENGTH: 27
<212> TYPE: DNA
<213> ORGANISM: Artificial sequence
<220> FEATURE:
<223> OTHER INFORMATION: PCR Primer

<400> SEQUENCE: 13
cgacaaaaat ctagataacg agggcaa                                           27

<210> SEQ ID NO 14
```

```
<211> LENGTH: 27
<212> TYPE: DNA
<213> ORGANISM: Artificial sequence
<220> FEATURE:
<223> OTHER INFORMATION: PCR Primer

<400> SEQUENCE: 14
ttcacttcac aggtcaagct tagttag                                      27

<210> SEQ ID NO 15
<211> LENGTH: 33
<212> TYPE: DNA
<213> ORGANISM: Artificial sequence
<220> FEATURE:
<223> OTHER INFORMATION: PCR Primer
<220> FEATURE:
<221> NAME/KEY: misc_feature
<222> LOCATION: (16)..(18)
<223> OTHER INFORMATION: n is a, c, g, or t

<400> SEQUENCE: 15
ggcatcccga tcatgnnnct gcaaagccgc aag                               33

<210> SEQ ID NO 16
<211> LENGTH: 33
<212> TYPE: DNA
<213> ORGANISM: Artificial sequence
<220> FEATURE:
<223> OTHER INFORMATION: PCR Primer
<220> FEATURE:
<221> NAME/KEY: misc_feature
<222> LOCATION: (16)..(18)
<223> OTHER INFORMATION: n is a, c, g, or t

<400> SEQUENCE: 16
cttgcggctt tgcagnnnca tgatcgggat gcc                               33

<210> SEQ ID NO 17
<211> LENGTH: 33
<212> TYPE: DNA
<213> ORGANISM: Artificial sequence
<220> FEATURE:
<223> OTHER INFORMATION: PCR Primer
<220> FEATURE:
<221> NAME/KEY: misc_feature
<222> LOCATION: (16)..(18)
<223> OTHER INFORMATION: n is a, c, g, or t

<400> SEQUENCE: 17
gggcgccagg acgcgnnnct cgatttccac aag                               33

<210> SEQ ID NO 18
<211> LENGTH: 33
<212> TYPE: DNA
<213> ORGANISM: Artificial sequence
<220> FEATURE:
<223> OTHER INFORMATION: PCR Primer
<220> FEATURE:
<221> NAME/KEY: misc_feature
<222> LOCATION: (16)..(18)
<223> OTHER INFORMATION: n is a, c, g, or t

<400> SEQUENCE: 18
cttgtggaaa tcgagnnncg cgtcctggcg ccc                               33

<210> SEQ ID NO 19
<211> LENGTH: 3246
<212> TYPE: DNA
<213> ORGANISM: Artificial sequence
```

<220> FEATURE:
<223> OTHER INFORMATION: pASK-IBA7

<400> SEQUENCE: 19

| | | | | | |
|---|---|---|---|---|---|
| ccatcgaatg | gccagatgat | taattcctaa | tttttgttga | cactctatca | ttgatagagt | 60 |
| tattttacca | ctccctatca | gtgatagaga | aaagtgaaat | gaatagttcg | acaaaaatct | 120 |
| agataacgag | ggcaaaaaat | ggctagctgg | agccacccgc | agttcgaaaa | atcgaaggg | 180 |
| cgccgagacc | gcggtcccga | attcgagctc | ggtacccggg | gatccctcga | ggtcgacctg | 240 |
| caggggacc | atggtctctg | atatctaact | aagcttgacc | tgtgaagtga | aaatggcgc | 300 |
| acattgtgcg | acatttttt | tgtctgccgt | ttaccgctac | tgcgtcacgg | atctccacgc | 360 |
| gccctgtagc | ggcgcattaa | gcgcggcggg | tgtggtggtt | acgcgcagcg | tgaccgctac | 420 |
| acttgccagc | gccctagcgc | ccgctccttt | cgctttcttc | ccttcctttc | tcgccacgtt | 480 |
| cgccggcttt | ccccgtcaag | ctctaaatcg | ggggctccct | ttagggttcc | gatttagtgc | 540 |
| tttacggcac | ctcgacccca | aaaaacttga | ttagggtgat | ggttcacgta | gtgggccatc | 600 |
| gccctgatag | acggtttttc | gccctttgac | gttggagtcc | acgttcttta | atagtggact | 660 |
| cttgttccaa | actggaacaa | cactcaaccc | tatctcggtc | tattcttttg | atttataagg | 720 |
| gattttgccg | atttcggcct | attggttaaa | aaatgagctg | atttaacaaa | aatttaacgc | 780 |
| gaattttaac | aaaatattaa | cgcttacaat | ttcaggtggc | acttttcggg | gaaatgtgcg | 840 |
| cggaacccct | atttgtttat | ttttctaaat | acattcaaat | atgtatccgc | tcatgagaca | 900 |
| ataaccctga | taaatgcttc | aataatattg | aaaaaggaag | agtatgagta | ttcaacattt | 960 |
| ccgtgtcgcc | cttattccct | tttttgcggc | attttgcctt | cctgttttg | ctcacccaga | 1020 |
| aacgctggtg | aaagtaaaag | atgctgaaga | tcagttgggt | gcacgagtgg | gttacatcga | 1080 |
| actggatctc | aacagcggta | agatccttga | gagttttcgc | cccgaagaac | gttttccaat | 1140 |
| gatgagcact | tttaaagttc | tgctatgtgg | cgcggtatta | tcccgtattg | acgccgggca | 1200 |
| agagcaactc | ggtcgccgca | tacactattc | tcagaatgac | ttggttgagt | actcaccagt | 1260 |
| cacagaaaag | catcttacgg | atggcatgac | agtaagagaa | ttatgcagtg | ctgccataac | 1320 |
| catgagtgat | aacactgcgg | ccaacttact | tctgacaacg | atcggaggac | cgaaggagct | 1380 |
| aaccgctttt | ttgcacaaca | tgggggatca | tgtaactcgc | cttgatcgtt | gggaaccgga | 1440 |
| gctgaatgaa | gccataccaa | acgacgagcg | tgacaccacg | atgcctgtag | caatggcaac | 1500 |
| aacgttgcgc | aaactattaa | ctggcgaact | acttactcta | gcttcccggc | aacaattgat | 1560 |
| agactggatg | gaggcggata | aagttgcagg | accacttctg | cgctcggccc | ttccggctgg | 1620 |
| ctggtttatt | gctgataaat | ctggagccgg | tgagcgtggc | tctcgcggta | tcattgcagc | 1680 |
| actggggcca | gatggtaagc | cctcccgtat | cgtagttatc | tacacgacgg | ggagtcaggc | 1740 |
| aactatggat | gaacgaaata | gacagatcgc | tgagataggt | gcctcactga | ttaagcattg | 1800 |
| gtaggaatta | atgatgtctc | gtttagataa | aagtaaagtg | attaacagcg | cattagagct | 1860 |
| gcttaatgag | gtcggaatcg | aaggtttaac | aacccgtaaa | ctcgcccaga | agctaggtgt | 1920 |
| agagcagcct | acattgtatt | ggcatgtaaa | aaataagcgg | gctttgctcg | acgccttagc | 1980 |
| cattgagatg | ttagataggc | accatactca | cttttgccct | ttagaagggg | aaagctggca | 2040 |
| agatttttta | cgtaataacg | ctaaaagttt | tagatgtgct | ttactaagtc | atcgcgatgg | 2100 |
| agcaaaagta | catttaggta | cacggcctac | agaaaaacag | tatgaaactc | tcgaaaatca | 2160 |
| attagccttt | ttatgccaac | aaggtttttc | actagagaat | gcattatatg | cactcagcgc | 2220 |

```
agtggggcat tttactttag gttgcgtatt ggaagatcaa gagcatcaag tcgctaaaga    2280
agaaagggaa acacctacta ctgatagtat gccgccatta ttacgacaag ctatcgaatt    2340
atttgatcac caaggtgcag agccagcctt cttattcggc cttgaattga tcatatgcgg    2400
attagaaaaa caacttaaat gtgaaagtgg gtcttaaaag cagcataacc tttttccgtg    2460
atggtaactt cactagttta aaaggatcta ggtgaagatc cttttttgata atctcatgac    2520 caaaatccct taacgtgagt tttcgttcca ctgagcgtca gacccgtag aaagatcaa     2580 aggatcttct tgagatcctt ttttttctgcg cgtaatctgc tgcttgcaaa caaaaaaacc    2640
accgctacca gcggtggttt gtttgccgga tcaagagcta ccaactcttt ttccgaaggt    2700
aactggcttc agcagagcgc agataccaaa tactgtcctt ctagtgtagc cgtagttagg    2760
ccaccacttc aagaactctg tagcaccgcc tacatacctc gctctgctaa tcctgttacc    2820
agtggctgct gccagtggcg ataagtcgtg tcttaccggg ttggactcaa gacgatagtt    2880
accggataag gcgcagcggt cgggctgaac ggggggttcg tgcacacagc ccagcttgga    2940
gcgaacgacc tacaccgaac tgagatacct acagcgtgag ctatgagaaa gcgccacgct    3000
tcccgaaggg agaaaggcgg acaggtatcc ggtaagcggc agggtcggaa caggagagcg    3060
cacgagggag cttccagggg gaaacgcctg gtatctttat agtcctgtcg ggtttcgcca    3120
cctctgactt gagcgtcgat ttttgtgatg ctcgtcaggg gggcggagcc tatggaaaaa    3180
cgccagcaac gcggcctttt tacggttcct ggccttttgc tggccttttg ctcacatgac    3240
ccgaca                                                              3246
```

<210> SEQ ID NO 20
<211> LENGTH: 30
<212> TYPE: DNA
<213> ORGANISM: Artificial sequence
<220> FEATURE:
<223> OTHER INFORMATION: PCR Primer

<400> SEQUENCE: 20
ggcgagaagc ttagaaatca tgatcgtcca                                     30

<210> SEQ ID NO 21
<211> LENGTH: 30
<212> TYPE: DNA
<213> ORGANISM: Artificial sequence
<220> FEATURE:
<223> OTHER INFORMATION: PCR Primer

<400> SEQUENCE: 21
ggatcctcta gagtctcact gcagcgcgcc                                     30

<210> SEQ ID NO 22
<211> LENGTH: 34
<212> TYPE: DNA
<213> ORGANISM: Artificial sequence
<220> FEATURE:
<223> OTHER INFORMATION: Primer Breu1499

<400> SEQUENCE: 22
tatacatatg atcgtccaac tgatcgccat cgtg                                34

<210> SEQ ID NO 23
<211> LENGTH: 40
<212> TYPE: DNA
<213> ORGANISM: Artificial sequence
<220> FEATURE:
<223> OTHER INFORMATION: Primer Breu1500

<400> SEQUENCE: 23
atttaagctt ttactgcagc gcgccggcct gcgtgacctc        40

<210> SEQ ID NO 24
<211> LENGTH: 11
<212> TYPE: PRT
<213> ORGANISM: Artificial sequence
<220> FEATURE:
<223> OTHER INFORMATION: Peptide sequence

<400> SEQUENCE: 24

Ala Ile Asp Ala Ile Phe Ala Pro Glu Gly Val
1               5                   10

<210> SEQ ID NO 25
<211> LENGTH: 287
<212> TYPE: PRT
<213> ORGANISM: Artificial sequence
<220> FEATURE:
<223> OTHER INFORMATION: Partial sequence of the clone LU2898
<220> FEATURE:
<221> NAME/KEY: misc_feature
<222> LOCATION: (158)..(175)
<223> OTHER INFORMATION: Xaa can be any naturally occurring amino acid

<400> SEQUENCE: 25

Ile Val Val Ala Leu Tyr Ala Val Leu Phe Ala Phe Thr Leu Phe Thr
1               5                   10                  15

Ala His Gln Val Arg Arg Phe Pro Pro Glu Gly Lys Phe Val Glu
            20                  25                  30

Ile Asp Gly Asp Arg Leu His Tyr Val Asp Tyr Gly Ser Gly Pro Pro
        35                  40                  45

Ile Val Met Val His Gly Leu Cys Gly Gln Leu Leu Asn Phe Ala Tyr
    50                  55                  60

Leu Asp Leu Ala Arg Leu Ala Gln Ser His Arg Val Ile Leu Val Asp
65                  70                  75                  80

Arg Ala Gly Ser Gly Arg Ser Thr Arg Gly Pro Ala Ser Arg Ala Asn
                85                  90                  95

Val Tyr Ala Gln Ala Arg Gly Ile Ala Arg Phe Ile Glu Thr Leu Gly
            100                 105                 110

Leu Glu Arg Pro Val Leu Val Gly His Ser Leu Gly Gly Ala Ile Ala
        115                 120                 125

Leu Ala Val Gly Leu Asp Tyr Pro Glu Arg Val Ser Arg Ile Ala Leu
    130                 135                 140

Ile Ala Pro Leu Thr His Thr Glu Thr Glu Pro Pro Lys Xaa Xaa Xaa
145                 150                 155                 160

Xaa Xaa Xaa Xaa Xaa Xaa Xaa Xaa Xaa Xaa Xaa Xaa Xaa Xaa Thr
                165                 170                 175

Met Gly Ile Pro Ile Met Ile Leu Gln Ser Arg Lys Ala Ile Asp Ala
            180                 185                 190

Ile Phe Ala Pro Glu Pro Val Pro Arg Asp Phe Pro Leu Lys Gly Gly
        195                 200                 205

Gly Met Met Gly Leu Arg Pro Glu Ala Phe Tyr Ala Ala Ser Ser Asp
    210                 215                 220

Leu Val Ala Ala Pro Glu Asp Leu Pro Asp Met Glu Arg Arg Tyr Pro
225                 230                 235                 240

Thr Leu Gly Val Pro Val Ser Met Leu Tyr Gly Arg Gln Asp Ala Ile
                245                 250                 255

```
Leu Asp Phe His Lys His Gly Glu Gly Leu Lys Arg Lys Leu Asp Gly
            260                 265                 270

Val Glu Leu Ser Ala Val Glu Gly Gly His Met Leu Pro Val Thr
        275                 280                 285
```

<210> SEQ ID NO 26
<211> LENGTH: 288
<212> TYPE: PRT
<213> ORGANISM: Artificial sequence
<220> FEATURE:
<223> OTHER INFORMATION: Partial sequence of the P. fluorescens enzyme

<400> SEQUENCE: 26

```
Val Leu Val Gly Ala Ser Val Val Phe Trp Gly Leu Ser Ala Trp Met
1               5                   10                  15

Thr Arg Arg Ile Glu Ala Ala Val Pro Gly Asn Gly Arg Phe Val Glu
            20                  25                  30

Val Asp Gly Glu Arg Phe His Tyr Tyr Glu Glu Gly Lys Gly Pro Pro
        35                  40                  45

Leu Val Met Ile His Gly Leu Met Gly Ser Ser Arg Asn Leu Thr Tyr
    50                  55                  60

Ala Leu Ser Arg Gln Leu Arg Glu His Phe Arg Val Ile Thr Leu Asp
65                  70                  75                  80

Arg Pro Gly Ser Gly Tyr Ser Thr Arg His Lys Gly Thr Ala Ala Asp
                85                  90                  95

Leu Pro Ala Gln Ala Arg Gln Val Ala Ala Phe Ile Asn Gln Leu Gly
            100                 105                 110

Leu Asp Lys Pro Leu Val Leu Gly His Ser Leu Gly Gly Ala Ile Ser
        115                 120                 125

Leu Ala Leu Ala Leu Asp His Pro Glu Ala Val Ser Gly Leu Val Leu
    130                 135                 140

Val Ala Pro Leu Thr His Pro Gln Pro Arg Leu Pro Leu Val Phe Trp
145                 150                 155                 160

Ser Leu Ala Val Arg Pro Ala Trp Leu Arg Arg Phe Val Ala Asn Thr
                165                 170                 175

Leu Thr Val Pro Met Gly Leu Leu Thr Arg Arg Ser Val Val Lys Gly
            180                 185                 190

Val Phe Ala Pro Asp Ala Ala Pro Glu Asp Phe Ala Thr Arg Gly Gly
        195                 200                 205

Gly Leu Leu Gly Met Arg Pro Asp Asn Phe Tyr Ala Ala Ser Ser Glu
    210                 215                 220

Ile Ala Leu Val Asn Asp Cys Leu Pro Gly Met Val Lys Arg Tyr Pro
225                 230                 235                 240

Gln Leu Ala Leu Pro Ile Gly Leu Ile Tyr Gly Ala Gln Asp Lys Val
                245                 250                 255

Leu Asp Phe Arg Arg His Gly Gln Ala Leu Ala Asp Lys Val Pro Gly
            260                 265                 270

Leu Lys Leu Gln Val Val Glu Gly Arg Gly His Met Leu Pro Ile Thr
        275                 280                 285
```

MUTANTS OF A PSEUDOMONAS GLUMAE BUTYNOL ESTERASE

RELATED APPLICATIONS

This application is a national stage application (under 35 U.S.C. 371) of PCT/EP2007/056367, filed Jun. 26, 2007, which claims benefit of European application 06013236.2, filed Jun. 27, 2006.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_13111_00113. The size of the text file is 33 KB, and the text file was created on Jan. 24, 2011.

The invention relates to novel proteins having esterase activity, to functional equivalents and mutants thereof, to nucleic acid sequences coding therefor, to expression cassettes, vectors and recombinant microorganisms; to methods for preparing said proteins and to the use thereof for enzymic, in particular enantioselective enzymic, ester hydrolysis or transesterification of organic esters.

BACKGROUND OF THE INVENTION

Esterases and lipases are hydrolases which can be employed in industrial processes for synthesizing optically active organic compounds and which are characterized by high substrate specificity. Through a mechanism similar to that of serine proteases, they can transfer acyl groups onto nucleophiles such as, for example, carbonyl groups or hydrolytically cleave ester bonds. Esterases, lipases and serine proteases share the catalytic triad, a sequence motif consisting of the amino acids Ser, His and Asp, where the carbonyl carbon atom is subject to nucleophilic attack by the active Ser, which, with participation of the other two amino acids, leads to a charge distribution. Esterases and lipases may also transfer acyl groups onto other nucleophiles, such as thioether thio groups or activated amines.

Lipases hydrolyze long-chain glycerol esters and are characterized by surface activation, i.e. the active site becomes accessible only in the presence of the lipid substrate. Lipases are stable in nonaqueous organic solvents and are employed in numerous industrial processes for kinetic racemate resolution, i.e. one enantiomer is converted substantially faster than the other. Said enantiomer can be subsequently obtained from the reaction solution owing to different physical and chemical properties.

Nakamura (Nakamura, K. et al., Tetrahedron; Asymmetry 9, (1999), 4429-4439) describes the racemate resolution of 1-alkyn-3-ol by transesterification in hydrophobic solvents with the aid of commercially available lipases (Amano AK, AH and PS; Amano Pharmaceuticals Co. Ltd.). In this reaction, enantioselectivity increases with the chain length of the acyl donor and sterically large residues (chloroacetate, vinyl benzoate) have an adverse effect on the reaction. Yang (Yang, H. et al., J. Org. Chem. 64, (1999), 1709-1712) describes the enantioselective preparation of optically active acids by transesterification with vinyl esters using lipase B from *Candida antarctica* as catalyst. In this case, ethyl esters lead to a distinctly lower reaction rate and selectivity. A lipase isolated from *Burkholderia plantarii* (*Pseudomonas plantarii* or *glumae*) DSM 6535 is employed for enantioselective acylation of racemic amities with the aid of ethyl methoxyacetate (Balkenhohl, F. et al., J. prakt. Chem. 339, (1997), 381-384).

Esterases enantioselectively catalyze the formation and breaking of ester bonds (forward and reverse reaction). Preference is given to using vinyl esters in the transesterification for obtaining optically active alcohols, since the alcohol function of the ester is no longer available after the conversion due to tautomerization to the aldehyde or ketone and thus the reverse reaction can be avoided. In contrast to lipases, esterases are not surface-activated and also convert organic compounds of relatively short chain length. Esterases of different substrate specificity have been isolated from various organisms.

Thus the esterase from *Pseudocardia thermophila* FERM-BP-6275 is used for hydrolyzing optically active chromanacetic esters (EP-A-0 892 044).

An esterase from *Bacillus acidocaldarius* hydrolyzes with low enantioselectivity esters from a narrow range of substrates (Manco, G. et al., Biochem. J. 332, (1998), 203-212).

Acylase 1 from *Aspergillus* is used for obtaining secondary alcohols by transesterification with vinyl esters in organic nonpolar solvents, it being preferred to convert secondary alcohols having short side chains (Faraldos, J. et al., Synlett 4, (1997), 367-370). From *Pseudomonas fluorescens* DSM 50 106 a membrane-bound lactone-specific esterase has been cloned (Khalameyzer, V. et al., Appl. and Environ. Microbial. 65(2), (1999), 477-482), and from the *E. coli* Q mutant an acetylesterase has been cloned (Peist, R. et al., J. Bacteriol. 179, (1997), 7679-7686). However, enantioselectivity and substrate specificity of these two esterases have not been studied in more detail. *Rhodococcus* sp. NCBM 11216 expresses 4 esterases, RR1 to RR4, which have different specificity. For the ester synthesis from naphthol and an acid, RR1 and RR2 prefer acids with short carbon chains, while RR3 and RR4 specifically convert acids having relatively long carbon chains and sterically relatively large residues (Gudelj, M. et al., J. Mol. Cat. B, Enzymatic 5, (1998), 261-266).

However, until recently esterases which possess a broad substrate range, have high enantioselectivity and can be employed in industrial processes have not been available for preparing small organic molecules such as optically active alcohols, acids or esters with short carbon chains.

WO-A-02/18560, for the first time, has described useful proteins having esterase activity, referred to as esterases therein, which are capable of enantioselective hydrolysis of a wide range of optically active esters. More specifically, it has described a protein comprising 510 amino acids (SEQ ID NO: 2) and the coding sequence thereof (SEQ ID NO: 1).

It is the object of the present invention to provide further optionally activity-optimized esterases which have at least one of the abovementioned properties.

SUMMARY OF THE INVENTION

Said object was surprisingly achieved by providing a protein having esterase activity or a functionally equivalent protein thereof, wherein said protein has a polypeptide chain with a total length of less than 510 amino acids and wherein said chain comprises at least one partial amino acid sequence according to SEQ ID NO: 3.

DESCRIPTION OF THE FIGURES

FIG. 1 depicts a sequence alignment of a partial amino acid sequence of butynol I esterase to a partial sequence of a lactone-specific esterase from *Pseudomonas fluorescens*.

Query: partial sequence of the clone of the invention, LU2898 (SEQ ID NO: 25). Sbjct: partial sequence of the *P. fluorescens* enzyme (Accession No.: 087637; SEQ ID NO: 26).

FIG. 2 illustrates the cloning chart for LU2898.

FIG. 3 depicts a comparison of the butynol esterase gene from LU2898 with the ERGO database. Regions of high homology are in dark. The text columns on the right-hand side are annotations from ERGO and indicate the corresponding e values; the e value is the probability of the sequence homology being based on chance. The position of the PstI cleavage site in the butynol esterase gene is indicated. For comparison, the amino acid sequence of the non-recombinant enzyme from *Ps. glumae* LU2023.

Figure 4:
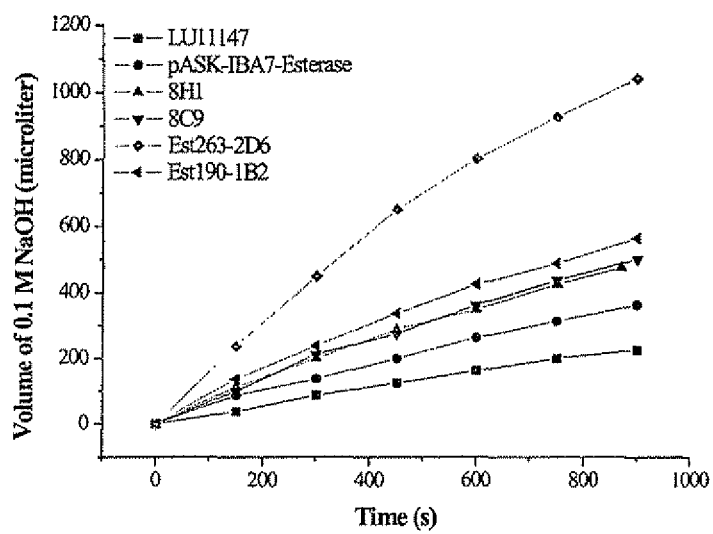

FIG. 4 illustrates the enzymic activity of an esterase of the invention having a sequence of 335 amino acids in length (from clone LU11147) and of activity-enhanced mutants derived therefrom.

DETAILED DESCRIPTION OF THE INVENTION

1. Preferred Embodiments

A first subject matter of the invention relates to a protein having esterase activity or a functionally equivalent protein thereof, wherein said protein has a polypeptide chain with a total length of less than 510 amino acids and wherein said chain comprises at least one partial amino acid sequence according to SEQ ID NO: 3, said protein preferably possessing an esterase activity which can be characterized by way of cleavage of the ester but-3-yn-2-yl butyrate as reference substrate.

Proteins of the invention may in particular additionally comprise at least one further partial amino acid sequence according to SEQ ID NO: 4, 5 or 6.

Said partial amino acid sequences according to SEQ ID NO: 3, 4, 5 or 6 are defined as follows (indicated in each case in the one-letter code of amino acids, with the first amino acid in each case corresponding to the particular amino-terminal end):

a)
FIETLGLERPVLVGHSLGGAIALAVGLDYPER,   (SEQ ID NO: 3)

b)
IALIAPLTHTETEP,                    (SEQ ID NO: 4)

c)
GGGMMGLRPEAFYAASSDLV               (SEQ ID NO: 5)

d)
AIDAIFAPEPV                        (SEQ ID NO: 6)

The proteins of the invention comprise in particular a polypeptide chain having less than 450, such as from 300 to 445 for example, or less than 350 amino acids, such as in particular from 345 to 300, in particular from about 330 to 340, especially 335, amino acids in total length.

Particular mention may be made of a protein comprising an amino acid sequence according to SEQ ID NO: 8.

The invention further relates to activity-enhanced mutants of these novel truncated esterases and also to similarly prepared mutants of the esterases disclosed in WO-A-02/18560 and comprising about 510 amino acids and functional equivalents thereof.

The invention relates in particular to esterase mutants having at least one functional mutation in any of the amino acid sequence regions 12-20, 185-195 and 258 to 268 of SEQ ID NO:2 or 8 and especially at least one functional mutation in any of the amino acid sequence positions 16, 190 and 263 of SEQ ID NO:2 or 8.

Nonlimiting examples of such mutations are the following amino acid substitutions: Leu16Pro, Ile190Thr, Ile190Arg and Ile263Val, either alone or in any combination.

The proteins of the invention are moreover a polypeptide chain having a calculated molecular weight of about 60 kDa or less, such as 56 kDa or less or 55.5 kDa or less, for example. For example, the truncated butynol esterases with fewer than 510 amino acids may have a molecular weight in the range from about 56 kDa to 20 kDa, for example from about 55.5 to 30 kDa or from 55.5 to 35 kDa or from 55.5 to 40 kDa or from 40 to 30 kDa, or from 55.5 to 45 kDa or from 38 to 34 kDa or from 36.5 to 35.5 kDa, for example.

Mutants of proteins according to SEQ ID NO: 2 preferably have calculated molecular weights in the range from about 60 to 40 kDa, or from 56 to 50 kDa or from 55.5 to 54 kDa.

Mutants of proteins according to SEQ ID NO: 8 preferably have calculated molecular weights in the range from about 38 to 34 kDa, from 37 to 35 kDa or from 36.5 to 35.5 kDa.

Preferred proteins can be obtained from *Pseudomonas glumae* (also referred to as *Burkholderia plantarii*) LU2023 with deposition number DSM 13176 (deposited with the DSMZ on Dec. 2, 1999) and, if appropriate, subsequent mutation.

The inventive proteins having esterase activity, functional equivalents and mutants moreover catalyze at least one of the following reactions:

a) enantioselective hydrolysis of optically active esters of the formula I

$$R^1\text{—COO—}R^2 \qquad\qquad (I),$$

in which
R$^1$ is a straight-chain or branched, optionally mono- or polysubstituted $C_1$-$C_{10}$-alkyl, $C_2$-$C_{10}$-alkenyl, $C_2$-$C_{10}$-alkynyl, and R$^2$ is a straight-chain or branched, optionally mono- or polysubstituted $C_1$-$C_{10}$-alkyl, $C_2$-$C_{10}$-alkenyl, $C_2$-$C_{10}$-alkynyl, $C_7$-$C_{15}$-aralkyl or a mono- or polynuclear, optionally mono- or polysubstituted aromatic radical,
R$^1$ and/or R$^2$ comprise at least one asymmetric carbon; and b) enantioselective transesterification of an ester of the formula I with an optically active alcohol of the formula II

$$R^2\text{—OH} \qquad\qquad (II),$$

in which R$^2$ has one of the above meanings and optionally has at least one asymmetric carbon.

Examples of suitable $C_1$-$C_{10}$-alkyl radicals, which may be mentioned, are straight-chain or branched radicals with from 1 to 10 carbons, such as methyl, ethyl, isopropyl or n-propyl, n-, iso-, sec- or tert-butyl, n-pentyl or isopentyl; moreover n-hexyl, n-heptyl, n-octyl, n-nonyl, n-decyl, and also the singly or multiply branched analogs thereof.

Examples of suitable $C_2$-$C_{10}$-alkenyl radicals are the mono-polyunsaturated analogs of the abovementioned alkyl radicals with from 2 to 10 carbons, which analogs preferably have one or two carbon-carbon double bonds which may be in any position of the carbon chain.

Examples of suitable $C_2$-$C_{10}$-alkynyl radicals are the mono- or polyunsaturated analogs of the abovementioned alkyl radicals with from 2 to 10 carbons, which analogs preferably have one or two carbon-carbon triple bonds which may be in any position of the carbon chain.

$C_7$-$C_{15}$-Aralkyl is preferably phenyl-$C_1$-$C_5$-alkyl or naphthyl-$C_1$-$C_5$-alkyl.

Examples of a mononuclear or polynuclear, optionally mono- or polysubstituted aromatic radical, which may be mentioned, are phenyl and naphthyl that are substituted with 1, 2 or 3 identical or different substituents selected from among $C_1$-$C_5$-alkyl such as methyl, ethyl, isopropyl or n-propyl, n-, iso-, sec- or tert-butyl, n-pentyl or isopentyl; hydroxy, mercapto, amino, nitro or halo such as F, Br, Cl.

The ester of the formula I is derived, for example, from straight-chain or branched, optionally mono- or polyunsaturated, optionally substituted $C_1$-$C_{11}$-monocarboxylic acids. Mention may be made by way of example of: saturated acids such as formic acid, acetic acid, propionic acid and n-butyric acid and i-butyric acid, n-valeric acid and isovaleric acid, caproic acid, enanthoic acid, caprylic acid, pelargonic acid, capric acid, undecanoic acid; monounsaturated acids such as acrylic acid, crotonic acid; and diunsaturated acids such as sorbic acid. If the acids comprise double bonds, then the latter may be both in cis and in trans form.

The invention furthermore relates to polynucleotides coding for a protein, a functional equivalent or a mutant as defined above, and to functional equivalents of said polynucleotides, polynucleotides complementary thereto and to the nucleic acid sequences hybridizable therewith.

The invention relates in particular to those polynucleotides comprising a nucleotide sequence of at least 30 consecutive nucleotide residues in a nucleic acid sequence according to SEQ ID NO: 7.

The invention moreover relates to a polynucleotide wherein the codon in the region corresponding to amino acid position 263 of SEQ ID NO: 8 is selected from among GTT and GTC.

The invention further relates to expression cassettes comprising at least one polynucleotide as defined above and operatively linked to at least one regulatory nucleic acid sequence.

The invention further relates to recombinant vectors for transforming a eukaryotic or prokaryotic host, comprising a polynucleotide as defined above or an expression cassette as defined above.

The invention further relates to a process for preparing a protein as defined above, which comprises culturing a microorganism which produces said protein endogenously or a microorganism transformed with a vector as defined above and isolating said protein from the culture.

Suitable processes in this connection use the microorganism *Pseudomonas glumae* (*Burkholderia plantarii*) LU2023 with deposition number DSM 13176 or a microorganism derived therefrom.

The invention also relates to a protein as defined above and to functional equivalents or mutants thereof, obtainable according to a process as defined above.

The invention furthermore relates to *Pseudomonas glumae* (*Burkholderia plantarii*) LU2023 with deposition number DSM 13176 and to variants and mutants thereof.

The invention moreover relates to microorganisms carrying a vector as defined above.

The invention furthermore relates to a process for enantioselective ester hydrolysis using a protein (including functional equivalents and mutants) as defined above, which process comprises
 a) contacting said protein with a stereoisomer mixture of an optically active ester of the formula I; and
 b) obtaining the optically active compounds produced by stereoselective hydrolysis of any of said stereoisomers and/or the nonhydrolyzed ester enantiomer from the reaction medium.

The invention also relates to a process for enantioselective transesterification, which comprises
 a) contacting a stereoisomer mixture of an optically active alcohol of the formula II with an ester of the formula I in the presence of a protein (including functional equivalents and mutants) as defined above and obtaining the unreacted alcohol stereoisomer from the reaction medium; or
 b) contacting a stereoisomer mixture of an optically active ester of the formula I with an alcohol of the formula II in the presence of a protein (including functional equivalents and mutants) as defined above and obtaining a stereoisomer of the optically active alcohol comprised in said ester from the reaction medium.

According to a particular variant of this process, the acylating agent for an optically active alcohol, which is used for transesterification, is a vinyl ester.

The invention in particular relates to a process as defined above, wherein the reaction medium used is an organic solvent.

2. Explanation of General Terms

An "esterase" or "butynol esterase" or "butynol I esterase" is an enzyme which catalyzes at least one of the enzymic conversions indicated herein, in particular at least cleavage of a reference butynol ester of a carboxylic acid, in particular of butyric acid, such as for example a butynol butyrate such as but-3yn-2yl butyrate.

A sequence "derived" from a specifically disclosed sequence or "homologous" thereto, for example a derived amino acid sequence or nucleic acid sequence, means according to the invention, unless indicated otherwise, a sequence which is at least 80% or at least 90%, in particular 91%, 92%, 93%, 94%, 95%, 96%, 97%, 98% and 99%, identical to the starting sequence.

"Identity" between two nucleic acids means identity of the nucleotides over the entire nucleic acid length in each case, in particular the identity calculated by comparison with the aid of the Vector NTI Suite 7.1 software from Informax (USA) using the Clustal method (Higgins D G, Sharp P M. Fast and sensitive multiple sequence alignments on a microcomputer. Comput Appl. Biosci. 1989 April; 5(2):151-1), setting the following parameters:

| Multiple alignment parameter: | |
| --- | --- |
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |
| Pairwise alignment parameter: | |
| FAST algorithm | on |
| K-tuple size | 1 |
| Gap penalty | 3 |
| Window size | 5 |
| Number of best diagonals | 5 |

3. Further Embodiments of the Invention

3.1 Proteins According to the Invention

The present invention is not limited to the specifically disclosed proteins and enzymes having esterase activity but rather extends also to functional equivalents thereof.

For the purposes of the present invention, "functional equivalents" or analogs of the specifically disclosed enzymes are polypeptides which differ from said enzymes and which furthermore possess the desired biological activity such as hydrolytic activity, for example.

"Functional equivalents", for example, mean enzymes whose activity in the esterase activity assay used is at least 1%, such as for example at least 10% or 20%, such as for example at least 50% or 75% or 90%, higher or lower than the activity of an enzyme comprising an amino acid sequence according to SEQ ID NO: 8. Moreover, functional equivalents are preferably stable between pH 4 to 10, with their optimal pH advantageously being in a range from pH 5 to 9, such as 6 to 8, for example, and their optimal temperature being in a range from 15° C. to 80° C. or 20° C. to 70° C.

The esterase activity may be detected with the aid of various known assays. Without being limited thereto, an assay may be mentioned using a reference substrate such as, for example, a butynol butyrate such as but-3yn-2yl butyrate, under standardized conditions (such as e.g. 20 mM substrate, 10 mM phosphate buffer, pH 7.4, T=20° C.).

"Functional equivalents" mean according to the invention in particular also "mutants" which have a different amino acid than the specifically mentioned one in at least one sequence position of the abovementioned amino acid sequences, but which nevertheless possess one of the abovementioned biological activities. "Functional equivalents" thus comprise the mutants obtainable by one or more amino acid additions, substitutions, deletions and/or inversions, it being possible for said modifications to occur in any sequence position as long as they lead to a mutant having the property profile of the invention. Functional equivalence exists in particular also when the reactivity patterns between mutant and unmodified polypeptide agree qualitatively, i.e., for example, identical substrates are converted at different rates. Examples of suitable amino acid substitutions are summarized in the following table:

| Original residue | Examples of substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Specific examples of individual sequence regions suitable for carrying out mutations according to the invention have already been defined above, namely: the amino acid sequence regions 12-20, 185-195 and 258 to 268 from SEQ ID NO:2 or 8, in particular the amino acid sequence positions 16, 190 and 263 of SEQ ID NO:2 or 8.

Specific examples of suitable amino acid substitutions are Leu16Pro, Ile190Thr, Ile190Arg and Ile263Val. Further modifications thereof may be provided readily by the skilled worker in knowledge of the teaching of the present invention.

"Functional equivalents" in the above sense are also "precursors" of the described polypeptides and also "functional derivatives" and "salts" of said polypeptides.

"Precursors" are in that case natural or synthetic precursors of the polypeptides with or without the desired biological activity.

The expression "salts" means salts of carboxyl groups as well as acid addition salts of amino groups of the protein molecules according to the invention. Salts of carboxyl groups can be produced in a manner known per se and comprise inorganic salts, for example sodium, calcium, ammonium, iron and zinc salts, and salts with organic bases, for example amines, such as triethanolamine, arginine, lysine, piperidine and the like. Acid addition salts, for example salts with mineral acids, such as hydrochloric acid or sulfuric acid and salts with organic acids, such as acetic acid and oxalic acid, are also covered by the invention.

"Functional derivatives" of polypeptides according to the invention can also be produced on functional amino acid side groups or at their N-terminal or C-terminal end using known techniques. Such derivatives comprise for example aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxy groups, produced by reaction with acyl groups.

"Functional equivalents" naturally also comprise polypeptides that can be obtained from other organisms, as well as naturally occurring variants. For example, areas of homologous sequence regions can be established by sequence comparison, and equivalent enzymes can be determined on the basis of the specific parameters of the invention.

"Functional equivalents" also comprise fragments, preferably individual domains or sequence motifs, of the polypeptides according to the invention, which for example display the desired biological function.

"Functional equivalents" are, moreover, fusion proteins, which have one of the polypeptide sequences stated above or functional equivalents derived therefrom and at least one further, functionally different, heterologous sequence in functional N-terminal or C-terminal linkage (i.e. without substantial mutual functional impairment of the fusion protein parts). Nonlimiting examples of such heterologous sequences are e.g. signal peptides, histidine anchors or enzymes.

"Functional equivalents" that are also included according to the invention are homologs of the specifically disclosed proteins. These possess at least 60%, preferably at least 75% in particular at least 85%, e.g. 90, 91, 92, 93, 94, 95, 96, 97, 98 or 99%, homology with one of the specifically disclosed amino acid sequences, calculated according to the algorithm of Pearson and Lipman, Proc. Natl. Acad, Sci. (USA) 85(8), 1988, 2444-2448. A percentage homology of a homologous polypeptide according to the invention means in particular the percentage identity of the amino acid residues based on the total length of one of the amino acid sequences specifically described herein.

In the case of a possible protein glycosylation, "functional equivalents" according to the invention comprise proteins of the type designated above in deglycosylated or glycosylated form as well as modified forms that can be obtained by altering the glycosylation pattern.

Homologs of the proteins or polypeptides according to the invention can be produced by mutagenesis, e.g. by point mutation, extension or truncation of the protein.

Homologs of the proteins according to the invention can be identified by screening combinatorial libraries of mutants, for example truncation mutants. For example, a variegated library of protein variants can be produced by combinatorial mutagenesis at the nucleic acid level, e.g. by enzymatic ligation of a mixture of synthetic oligonucleotides. There are a great many methods that can be used for the production of libraries of potential homologs from a degenerated oligonucleotide sequence. Chemical synthesis of a degenerated gene sequence can be carried out in an automatic DNA synthesizer, and the synthetic gene can then be ligated into a suitable expression vector. The use of a degenerated set of genes makes it possible to supply all sequences in a mixture, which code for the desired set of potential protein sequences. Methods of synthesis of degenerated oligonucleotides are known to a person skilled in the art (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

In the prior art, several techniques are known for the screening of gene products of combinatorial libraries, which have been produced by point mutations or truncation, and for the screening of cDNA libraries for gene products with a selected property. These techniques can be adapted for the rapid screening of the gene libraries that have been produced by combinatorial mutagenesis of homologs according to the invention. The techniques most frequently used for the screening of large gene libraries, which are based on a high-throughput analysis, comprise cloning of the gene library in expression vectors that can be replicated, transformation of suitable cells with the resultant vector library and expression of the combinatorial genes in conditions in which detection of the desired activity facilitates isolation of the vector that codes for the gene whose product was detected. Recursive Ensemble Mutagenesis (REM), a technique that increases the frequency of functional mutants in the libraries, can be used in combination with the screening assays, in order to identify homologs (Arkin and Yourvan (1992) PNAS 89:7811-7815; Delgrave et al. (1993) Protein Engineering 6(3):327-331).

Further examples of functional equivalents of the esterases according to the invention comprise, for example, at least one partial sequence derived from SEQ ID NO: 3, 4, 5 or 6, with one or more amino acids having been substituted, deleted, inverted or added compared to the specifically indicated partial sequence and with the esterase activity differing from the esterase activity of the native protein by no more than ±90% or ±50%, preferably by no more than ±30%.

The esterases according to the invention are obtainable in particular from *Pseudomonas glumae* LU2023, deposition number DSM 13176. Further strain variants are available, for example starting from *Pseudomonas glumae* LU8093, by selection, for example by way of culturing on minimal medium plates with ethylphenyl acetate as the sole carbon source.

3.2 Coding Nucleic Acid Sequences

The invention also relates to nucleic acid sequences that code for an enzyme with esterase activity. Nucleic acid sequences comprising a sequence according to SEQ ID NO: 7; or a nucleic acid sequence derived from the amino acid sequence according to SEQ ID NO.: 8 are preferred.

All the nucleic acid sequences mentioned herein (single-stranded and double-stranded DNA and RNA sequences, for example cDNA and mRNA) can be produced in a manner known per se by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), Molecular Cloning: A laboratory manual, Cold Spring Harbor Laboratory Press.

The invention also relates to nucleic acid sequences (single-stranded and double-stranded DNA and RNA sequences, e.g. cDNA and mRNA), coding for any of the above polypeptides and their functional equivalents, which can be obtained for example using artificial nucleotide analogs.

The invention relates both to isolated nucleic acid molecules, which code for polypeptides or proteins according to the invention or biologically active segments thereof, and to nucleic acid fragments, which can be used for example as hybridization probes or primers for identifying or amplifying coding nucleic acids according to the invention.

The nucleic acid molecules according to the invention can in addition comprise untranslated sequences from the 3' and/or 5' end of the coding genetic region.

The invention further relates to the nucleic acid molecules that are complementary to the specifically described nucleotide sequences or a segment thereof.

The nucleotide sequences according to the invention make possible the production of probes and primers that can be used for the identification and/or cloning of homologous sequences in other cell types and organisms. Such probes and primers generally comprise a nucleotide sequence region which hybridizes under "stringent" conditions (see below) to at least about 12, preferably at least about 25, for example about 40, 50 or 75, consecutive nucleotides of a sense strand of a nucleic acid sequence according to the invention or of a corresponding antisense strand.

An "isolated" nucleic acid molecule is removed from other nucleic acid molecules that are present in the natural source of the nucleic acid and can moreover be essentially free from other cellular material or culture medium, if it is being produced by recombinant techniques, or can be free from chemical precursors or other chemicals, if it is being synthesized chemically.

A nucleic acid molecule according to the invention can be isolated by means of standard techniques of molecular biology and the sequence information supplied according to the invention. For example, cDNA can be isolated from a suitable cDNA library, using one of the specifically disclosed complete sequences or a segment thereof as hybridization probe and standard hybridization techniques (as described for example in Sambrook, J., Fritsch, E. F. and Maniatis, T. Molecular Cloning: A Laboratory Manual. 2nd edition, Cold Spring Harbor Laboratory, Cold Spring Harbor Laboratory Press, Cold Spring Harbor, N.Y., 1989). In addition, a nucleic acid molecule comprising one of the disclosed sequences or a segment thereof, can be isolated by the polymerase chain reaction, using the oligonucleotide primers that were constructed on the basis of this sequence. The nucleic acid amplified in this way can be cloned into a suitable vector and can be characterized by DNA sequence analysis. The oligonucleotides according to the invention can also be produced by standard methods of synthesis, e.g. using an automatic DNA synthesizer.

Nucleic acid sequences according to the invention, such as SEQ ID No: 7 or derivatives thereof, homologs or parts of these sequences, can for example be isolated by usual hybridization techniques or the PCR technique from other bacteria, e.g. via genomic or cDNA libraries. These DNA sequences hybridize in standard conditions with the sequences according to the invention.

"Hybridize" means the ability of a polynucleotide or oligonucleotide to bind to an almost complementary sequence in standard conditions, whereas nonspecific binding does not occur between noncomplementary partners in these conditions. For this, the sequences can be 90-100% complementary. The property of complementary sequences of being able to bind specifically to one another is utilized for example in Northern blotting or Southern blotting or in primer binding in PCR or RT-PCR.

Short oligonucleotides of the conserved regions are used advantageously for hybridization. However, it is also possible to use longer fragments of the nucleic acids according to the invention or the complete sequences for the hybridization. These standard conditions vary depending on the nucleic acid used (oligonucleotide, longer fragment or complete sequence) or depending on which type of nucleic acid—DNA or RNA—is used for hybridization. For example, the melting temperatures for DNA:DNA hybrids are approx. 10° C. lower than those of DNA:RNA hybrids of the same length.

For example, depending on the particular nucleic acid, standard conditions mean temperatures between 42 and 58° C. in an aqueous buffer solution with a concentration of from 0.1 to 5×SSC (1×SSC=0.15 M NaCl, 15 mM sodium citrate, pH 7.2) or additionally in the presence of 50% formamide, for example 42° C. in 5×SSC, 50% formamide. Advantageously, the hybridization conditions for DNA:DNA hybrids are 0.1× SSC and temperatures of from about 20° C. to 45° C., preferably between about 30° C. to 45° C. For DNA:RNA hybrids the hybridization conditions are advantageously 0.1×SSC and temperatures of from about 30° C. to 55° C., preferably from about 45° C. to 55° C. These stated temperatures for hybridization are examples of calculated melting temperature values for a nucleic acid with a length of approx. 100 nucleotides and a G+C content of 50% in the absence of formamide. The experimental conditions for DNA hybridization are described in relevant genetics textbooks, for example Sambrook et al., "Molecular Cloning", Cold Spring Harbor Laboratory, 1989, and can be calculated using formulas that are known by a person skilled in the art, for example depending on the length of the nucleic acids, the type of hybrids or the G+C content. A person skilled in the art can obtain further information on hybridization from the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

"Hybridization" can in particular be carried out under stringent conditions. Such hybridization conditions are for example described in Sambrook, J., Fritsch, E. F., Maniatis, T., in: Molecular Cloning (A Laboratory Manual), 2nd edition, Cold Spring Harbor Laboratory Press, 1989, pages 9.31-9.57 or in Current Protocols in Molecular Biology, John Wiley & Sons, N.Y. (1989), 6.3.1-6.3.6.

"Stringent" hybridization conditions mean in particular: incubation at 42° C. overnight in a solution consisting of 50% formamide, 5×SSC (750 mM NaCl, 75 mM trisodium citrate), 50 mM sodium phosphate (pH 7.6), 5×Denhardt's solution, 10% dextran sulfate and 20 g/ml denatured, sheared salmon sperm DNA, followed by washing of the filters with 0.1×SSC at 65° C.

The invention also relates to derivatives of the specifically disclosed or derivable nucleic acid sequences.

Thus, further nucleic acid sequences according to the invention can be derived e.g. from SEQ ID NO: 7 and can differ therefrom by addition, substitution, insertion or deletion of single or multiple nucleotides, but still code for polypeptides with the desired profile of properties.

The invention also encompasses nucleic acid sequences that comprise "silent" mutations or have been altered, in comparison with a specifically stated sequence, according to the codon usage of a special source or host organism, as well as naturally occurring variants, e.g. splicing variants or allelic variants, thereof.

It also relates to sequences that can be obtained by conservative nucleotide substitutions (i.e. the amino acid in question is replaced by an amino acid of the same charge, size, polarity and/or solubility).

The invention also relates to the molecules derived from the specifically disclosed nucleic acids by sequence polymorphisms. These genetic polymorphisms can exist between individuals within a population owing to natural variation. These natural variations usually produce a variance of 1 to 5% in the nucleotide sequence of a gene.

Derivatives of the nucleic acid sequence with the sequence SEQ ID NO: 7 according to the invention mean for example allelic variants having at least 60% homology at the level of the derived amino acids, preferably at least 80% homology, very particularly preferably at least 90% homology, over the entire sequence range (regarding homology at the amino acid level, reference should be made to the details given above for the polypeptides). Advantageously, the homologies can be higher over partial regions of the sequences.

Furthermore, derivatives are also to be understood to be homologs of the nucleic acid sequences according to the invention, in particular of SEQ ID NO: 7, for example fungal or bacterial homologs, truncated sequences, single-stranded DNA or RNA of the coding and noncoding DNA sequences. For example, homologs of SEQ ID NO: 7 have, at the DNA level, a homology of at least 40%, preferably of at least 60%, particularly preferably of at least 70%, very preferably of at least 80%, over the entire DNA region given in SEQ ID NO: 7.

Moreover, derivatives are to be understood to be, for example, fusions with promoters. The promoters that are upstream of the stated nucleotide sequences can be modified by at least one nucleotide exchange, at least one insertion, inversion and/or deletion, though without, however, impairing the functionality or efficacy of the promoters. Moreover, the efficacy of the promoters can be increased by altering their sequence or they can be replaced completely with more effective promoters, even of organisms of a different genus.

3.3 Constructs According to the Invention

The invention also relates to expression constructs, comprising, under the genetic control of regulatory nucleic acid sequences, a nucleic acid sequence coding for a polypeptide according to the invention; as well as vectors comprising at least one of these expression constructs.

"Expression unit" means, according to the invention, a nucleic acid with expression activity, which comprises a promoter as defined herein and, after functional linkage to a nucleic acid that is to be expressed or a gene, regulates expression, i.e. transcription and translation of this nucleic acid or of this gene. In this context, therefore, it is also called a "regulatory nucleic acid sequence". In addition to the promoter, other regulatory elements may be present, e.g. enhancers.

"Expression cassette" or "expression construct" means, according to the invention, an expression unit which is functionally linked with the nucleic acid that is to be expressed or the gene that is to be expressed. In contrast to an expression unit, an expression cassette thus comprises not only nucleic acid sequences which regulate transcription and translation, but also the nucleic acid sequences which should be expressed as protein as a result of transcription and translation.

The terms "expression" or "overexpression" describe, in the context of the invention, production of or increase in intracellular activity of one or more enzymes in a microorganism, which are encoded by the corresponding DNA. For this, it is possible for example to insert a gene in an organism, replace an existing gene with another gene, increase the number of copies of the gene or genes, use a strong promoter or use a gene that codes for a corresponding enzyme with high activity, and optionally these measures can be combined.

Preferably such constructs according to the invention comprise a promoter 5' upstream from the respective coding sequence, and a terminator sequence 3' downstream, and optionally further usual regulatory elements, in each case operatively linked to the coding sequence.

A "promoter", a "nucleic acid with promoter activity" or a "promoter sequence" mean, according to the invention, a nucleic acid which, functionally linked to a nucleic acid that is to be transcribed, regulates transcription of this nucleic acid.

"Functional" or "operative" linkage means, in this context, for example the sequential arrangement of one of the nucleic acids with promoter activity and a nucleic acid sequence that is to be transcribed and optionally further regulatory elements, for example nucleic acid sequences that ensure transcription of nucleic acids, and for example a terminator, in such a way that each of the regulatory elements can fulfill its function during transcription of the nucleic acid sequence. This does not necessarily require a direct linkage in the chemical sense. Genetic control sequences, such as enhancer sequences, for example, can also act on the target sequence from more remote positions or even from other DNA molecules. Arrangements are preferred in which the nucleic acid sequence that is to be transcribed is positioned downstream (i.e. at the 3' end) of the promoter sequence, so that the two sequences are bound covalently to one another. The distance between the promoter sequence and the nucleic acid sequence that is to be expressed transgenically can be less than 200 base pairs, or less than 100 base pairs or less than 50 base pairs.

Apart from promoters and terminators, examples of other regulatory elements that may be mentioned are targeting sequences, enhancers, polyadenylation signals, selectable markers, amplification signals, origins of replication and the like. Suitable regulatory sequences are described for example in Goeddel, Gene Expression Technology: Methods in Enzymology 185, Academic Press, San Diego, Calif. (1990).

Nucleic acid constructs according to the invention comprise in particular sequence SEQ ID NO: 7 or derivatives and homologs thereof, as well as the nucleic acid sequences that can be derived from SEQ ID NO: 8, which have advantageously been linked operatively or functionally to one or more regulatory signals for controlling, e.g. increasing, gene expression.

In addition to these regulatory sequences, the natural regulation of these sequences can still be present upstream of the actual structural genes and optionally can have been altered genetically, so that natural regulation has been switched off and expression of the genes has been increased. The nucleic acid construct can, however, also be of a simpler design, i.e. without any additional regulatory signals being inserted upstream of the coding sequence (e.g. SEQ ID NO: 7 or its homologs) and without removing the natural promoter with its regulation. Instead, the natural regulatory sequence is mutated so that regulation no longer takes place and gene expression is increased.

A preferred nucleic acid construct advantageously also comprises one or more of the aforementioned enhancer sequences, functionally linked to the promoter, which permit increased expression of the nucleic acid sequence. Additional advantageous sequences, such as other regulatory elements or terminators, can also be inserted at the 3' end of the DNA sequences. One or more copies of the nucleic acids according to the invention can be comprised in the construct. The construct can also comprise other markers, such as antibiotic resistances or auxotrophy-complementing genes, optionally for selection for the construct.

Examples of suitable regulatory sequences are comprised in promoters such as cos, tac, trp, tet, trp-tet, lpp, lac, lpp-lac, lacI$^q$, T7, T5, T3, gal, trc, ara, rhaP (rhaP$_{BAD}$)SP6, lambda-P$_R$ or in the lambda-P$_L$ promoter, which are employed advantageously in Gram-negative bacteria. Other advantageous regulatory sequences are comprised for example in the Gram-positive promoters amy and SPO2, in the yeast or fungal promoters ADC1, MFalpha, AC, P-60, CYC1, GAPDH, TEF, rp28, ADH. Artificial promoters can also be used for regulation.

For expression, the nucleic acid construct is inserted in a host organism advantageously into a vector, for example a plasmid or a phage, which permits optimum expression of the genes in the host. In addition to plasmids and phages, vectors are also to be understood as meaning all other vectors known to a person skilled in the art, i.e. for example viruses, such as SV40, CMV, baculovirus and adenovirus, transposons, IS elements, phasmids, cosmids, and linear or circular DNA. These vectors can be replicated autonomously in the host organism or can be replicated chromosomally. These vectors represent a further embodiment of the invention.

Suitable plasmids are, for example in *E. coli*, pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, λgt11 or pBdCl; in *Streptomyces* pIJ101, pIJ364, pIJ702 or pIJ361; in *Bacillus* pUB110, pC194 or pBD214; in *Corynebacterium* pSA77 or pAJ667; in fungi pALS1, pIL2 or pBB116; in yeasts 2alphaM, pAG-1, YEp6, YEp13 or pEMBLYe23 or in plants pLGV23, pGHlac$^+$, pBIN19, pAK2004 or pDH51. The aforementioned plasmids represent a small selection of the possible plasmids. Other plasmids are well known to a person skilled in the art and will be found for example in the book Cloning Vectors (Eds. Pouwels P. H. et al. Elsevier, Amsterdam-New York-Oxford, 1985, ISBN 0 444 904018).

In a further embodiment of the vector, the vector comprising the nucleic acid construct according to the invention or the nucleic acid according to the invention can also be introduced advantageously in the form of a linear DNA to the microorganisms and integrated into the genome of the host organism through heterologous or homologous recombination. This linear DNA can comprise a linearized vector such as a plasmid or just the nucleic acid construct or the nucleic acid according to the invention.

For optimum expression of heterologous genes in organisms, it is advantageous to alter the nucleic acid sequences in accordance with the specific codon usage employed in the organism. The codon usage can easily be determined on the basis of computer evaluations of other, known genes of the organism in question.

The production of an expression cassette according to the invention is based on fusion of a suitable promoter to a suitable coding nucleotide sequence and a terminator signal or polyadenylation signal. Common recombination and cloning techniques are used for this, as described for example in T. Maniatis, E. F. Fritsch and J. Sambrook, Molecular Cloning: A Laboratory Manual, Cold Spring Harbor Laboratory, Cold Spring Harbor, N.Y. (1989) as well as in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

The recombinant nucleic acid construct or gene construct is inserted advantageously in a host-specific vector for expression in a suitable host organism, which enables the genes to be optimally expressed in the host. Vectors are well known to a person skilled in the art and can be found for example in "Cloning Vectors" (Pouwels P. H. et al., Publ. Elsevier, Amsterdam-New York-Oxford, 1985).

3.4 Microorganisms that can be Used According to the Invention

Depending on the context, the term "microorganism" means the starting microorganism (wild-type) or a genetically modified, recombinant microorganism, or both.

By means of the vectors according to the invention, recombinant microorganisms can be produced, which have been transformed for example with at least one vector according to the invention and can be used for production of the polypeptides according to the invention. Advantageously, the recombinant constructs according to the invention, described above, are inserted in a suitable host system and expressed. Preferably, common cloning and transfection methods that are familiar to a person skilled in the art are used, for example co-precipitation, protoplast fusion, electroporation, retroviral transfection and the like, in order to secure expression of the stated nucleic acids in the particular expression system. Suitable systems are described for example in Current Protocols in Molecular Biology, F. Ausubel et al., Publ. Wiley Interscience, New York 1997, or Sambrook et al. Molecular Cloning: A Laboratory Manual. 2nd edition, Cold Spring Harbor Laboratory, Cold Spring Harbor Laboratory Press, Cold Spring Harbor, N.Y., 1989.

In principle, all prokaryotic or eukaryotic organisms can be considered as recombinant host organisms for the nucleic acid according to the invention or the nucleic acid construct. Microorganisms such as bacteria, fungi or yeasts are used advantageously as host organisms. It is advantageous to use Gram-positive or Gram-negative bacteria, preferably bacteria of the families Enterobacteriaceae, Pseudomonadaceae, Rhizobiaceae, Streptomycetaceae or Nocardiaceae, especially preferably bacteria of the genera *Escherichia, Pseudomonas, Streptomyces, Nocardia, Burkholderia, Salmonella, Agrobacterium* or *Rhodococcus*. The genus and species *Escherichia coli* is very particularly preferred. Other advantageous bacteria can also be found in the following group: alpha-proteobacteria, beta-proteobacteria or gamma-proteobacteria.

The host organism or host organisms according to the invention preferably comprise here at least one of the nucleic acid sequences, nucleic acid constructs or vectors described in this invention, which code for an enzyme with esterase activity as defined above.

The organisms used in the process according to the invention are grown or bred in a manner familiar to a person skilled in the art, depending on the host organism. As a rule, microorganisms are grown in a liquid medium, which comprises a source of carbon, generally in the form of sugars, a source of nitrogen generally in the form of organic sources of nitrogen such as yeast extract or salts such as ammonium sulfate, trace elements such as iron, manganese and magnesium salts and if appropriate vitamins, at temperatures between 0° C. and 100° C., preferably from 10° C. to 60° C., with oxygen aeration. The pH of the liquid nutrient medium can be maintained at a fixed value, i.e. regulated or not regulated during growing. Growing can be carried out batchwise, semi-batchwise or continuously. Nutrients can be supplied at the start of fermentation or can be supplied subsequently, either semi-continuously or continuously. The ketone can be added directly during growing, or advantageously after growing. The enzymes can be isolated from the organisms by the process described in the examples or can be used as crude extract for the reaction.

3.5 Recombinant Production of the Esterase:

The invention also relates to processes for recombinant production of polypeptides according to the invention or functional, biologically active fragments thereof, by cultivating a polypeptide-producing microorganism, if appropriate inducing expression of the polypeptides and isolating them from the culture. The polypeptides can also be produced on an industrial scale in this way, if so desired.

The microorganisms produced according to the invention can be cultured continuously or batchwise in a batch process or in a fed batch or repeated fed batch process. A review of known culturing methods will be found in the textbook by Chmiel (Bioprocesstechnik 1. Einfuhrung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)).

The culture medium that is to be used must satisfy the requirements of the particular strains in an appropriate manner. Descriptions of culture media for various microorganisms are given in the handbook "Manual of Methods for General Bacteriology" of the American Society for Bacteriology (Washington D.C., USA, 1981).

These media that can be used according to the invention generally comprise one or more sources of carbon, sources of nitrogen, inorganic salts, vitamins and/or trace elements.

Preferred sources of carbon are sugars, such as mono-, di- or polysaccharides. Very good sources of carbon are for example glucose, fructose, mannose, galactose, ribose, sorbose, ribulose, lactose, maltose, sucrose, raffinose, starch or cellulose. Sugars can also be added to the media via complex compounds, such as molasses, or other by-products from sugar refining. It may also be advantageous to add mixtures of various sources of carbon. Other possible sources of carbon are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid.

Sources of nitrogen are usually organic or inorganic nitrogen compounds or materials comprising these compounds. Examples of sources of nitrogen include ammonia gas or ammonium salts, such as ammonium sulfate, ammonium chloride, ammonium phosphate, ammonium carbonate or ammonium nitrate, nitrates, urea, amino acids or complex sources of nitrogen, such as corn-steep liquor, soybean flour, soybean protein, yeast extract, meat extract and others. The sources of nitrogen can be used separately or as a mixture.

Inorganic salt compounds that may be present in the media comprise the chloride, phosphate or sulfate salts of calcium, magnesium, sodium, cobalt, molybdenum, potassium, manganese, zinc, copper and iron.

Inorganic sulfur-containing compounds, for example sulfates, sulfites, dithionites, tetrathionates, thiosulfates, sulfides, but also organic sulfur compounds, such as mercaptans and thiols, can be used as sources of sulfur.

Phosphoric acid, potassium dihydrogen phosphate or dipotassium hydrogen phosphate or the corresponding sodium-containing salts can be used as sources of phosphorus.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention usually also comprise other growth factors, such as vitamins or growth promoters, which include for example biotin, riboflavin, thiamine, folic acid, nicotinic acid, pantothenate and pyridoxine. Growth factors and salts often come from complex components of the media, such as yeast extract, molasses, corn-steep liquor and the like. In addition, suitable precursors can be added to the culture medium. The precise composition of the compounds in the medium is strongly dependent on the particular experiment and must be decided individually for each specific case. Information on media optimization can be found in the textbook "Applied Microbiol. Physiology, A Practical Approach" (Publ. P. M. Rhodes, P. F. Stanbury, IRL Press (1997) p. 53-73, ISBN 0 19 963577 3). Growth media can also be obtained from commercial suppliers, such as Standard 1 (Merck) or BHI (Brain heart infusion, DIFCO) etc.

All media components are sterilized, either by heating (20 min at 1.5 bar and 121° C.) or by sterile filtration. The components can be sterilized either together, or if necessary separately. All the components of the medium can be present at the start of growing, or optionally can be added continuously or by batch feed.

The temperature of the culture is normally between 15° C. and 45° C., preferably from 25° C. to 40° C. and can be kept constant or can be varied during the experiment. The pH of the medium should be in the range from 5 to 8.5, preferably around 7.0. The pH for growing can be controlled during growing by adding basic compounds such as sodium hydroxide, potassium hydroxide, ammonia or ammonia water or acid compounds such as phosphoric acid or sulfuric acid. Antifoams, e.g. fatty acid polyglycol esters, can be used for controlling foaming. To maintain the stability of plasmids, suitable substances with selective action, e.g. antibiotics, can be added to the medium. Oxygen or oxygen-containing gas mixtures, e.g. ambient air, are fed into the culture in order to maintain aerobic conditions. The temperature of the culture is normally from 20° C. to 45° C. Culture is continued until a maximum of the desired product has formed. This is normally achieved within 10 hours to 160 hours.

The fermentation broth is then processed further. Depending on the requirements, the biomass can be removed completely or partially from the fermentation broth by separation techniques, e.g. centrifugation, filtration, decanting or a combination of these methods, or can be left in the fermentation broth completely.

If the polypeptides are not secreted into the culture medium, the cells may also be disrupted and the product can be obtained from the lysate by known techniques for isolating proteins. The cells can be disrupted optionally by high-frequency ultrasound, by high pressure, e.g. in a French pressure cell, by osmolysis, by the action of detergents, lytic enzymes or organic solvents, by means of homogenizers or by a combination of several of the methods listed.

The polypeptides can be purified using known chromatographic methods, such as molecular sieve chromatography (gel filtration), Q-Sepharose chromatography, ion exchange chromatography and hydrophobic chromatography, and by other usual methods such as ultrafiltration, crystallization, salting-out, dialysis and native gel electrophoresis. Suitable methods are described for example in Cooper, F. G., Biochemische Arbeitsmethoden, Verlag Walter de Gruyter, Berlin, N.Y. or in Scopes, R., Protein Purification, Springer Verlag, New York, Heidelberg, Berlin.

For isolating the recombinant protein it may be advantageous to use vector systems or oligonucleotides, which extend the cDNA by defined nucleotide sequences and therefore code for modified polypeptides or fusion proteins, which can be used e.g. for simpler purification. Suitable modifications of this kind are for example so-called "tags" which function as anchors, e.g. the modification known as the hexahistidine anchor, or epitopes that can be recognized as antigens by antibodies (described for example in Harlow, E. and Lane, D., 1988, Antibodies: A Laboratory Manual. Cold Spring Harbor (N.Y.) Press). These anchors can provide adhesion of the proteins to a solid support, e.g. a polymer matrix, for example for packing a chromatographic column, or can be used on a microtiter plate or on some other support.

At the same time, these anchors can also be used for recognition of the proteins. For recognition of the proteins it is also possible to use ordinary markers, such as fluorescent dyes and enzyme markers which form a detectable reaction product after reaction with a substrate, or radioactive markers, alone or in combination with the anchors for derivatization of the proteins.

3.6 Applications According to the Invention of the Esterases

The invention also relates to processes for enantioselective ester hydrolysis using the esterase, which processes comprise contacting the esterase with a stereoisomer mixture of an optically active ester of the formula I and obtaining the optically active compounds produced by stereoselective hydrolysis of any of the two stereoisomers and/or the nonhydrolyzed ester enantiomer from the reaction medium. It is, however, also possible for the esterase to hydrolyze those esters of the formula I which are not optically active.

The invention also relates to processes for enantioselective transesterification, which comprises contacting a stereoisomer mixture of an optically active alcohol of the formula II with an ester of the formula I in the presence of the esterase, and obtaining the unreacted alcohol stereoisomer from the reaction medium, or contacting a stereoisomer mixture of an optically active ester of the formula I with an alcohol of the formula II in the presence of said esterase, and obtaining a stereoisomer of the optically active alcohol comprised in said ester from the reaction medium. Vinyl esters are preferably used in transesterification as acylating agents for an optically active alcohol. This is advantageous because, after the conversion, the alcohol function of the vinyl ester is no longer available for the reverse reaction due to tautomerization. The esterase also catalyzes transesterification processes in which neither the ester nor the alcohol is optically active.

Preferred substrates of ester hydrolysis are esters of ethanol, propanol, butanol and, particularly preferably, butynol esters (butynol esters, esters of 1-methylprop-2-ynol) with carboxylic acids such as, for example, acetic acid, propionic acid, butyric acid, pentanoic acid, hexanoic acid, heptanoic acid, octanoic acid, lactic acid, 2-ethylhexanoic acid, 3-methylbutyric acid, methoxyacetic acid, 2-methylpropionic acid, 2-butenoic acid, 3-chloropropionic acid and 2-methylpentanoic acid. Particular preference is given to butynyl butyrate and butynyl methylbutyrate.

Preferred alcohols in the transesterification are ethanol, propanol and butanol, particularly preferred is butynol.

Preferred esters in the transesterification are vinyl esters such as, for example, vinyl acetate, vinyl propionate and vinyl butyrate.

Reaction media used in the above methods are organic solvents such as, for example, alkanes, ethers, toluene, dioxane, methyl isobutyl ketone, methyl tert-butyl ether (MTBE) and the like. In the ester hydrolysis, mixtures made from the buffer solution used and organic solvents such as, for example, MTBE and heptane or toluene may also be used.

Racemate resolution, i.e. enantioselectivity, and reaction rate can be influenced via size and hydrophobicity of the acid moiety.

The reaction according to the invention is preferably carried out at room temperature at from pH 6 to 9, particularly preferably at from pH 7.0 to 7.4. The esterase may be employed in the form of isolated or purified enzyme, as cells of the microorganism expressing the esterase, as culture supernatant, cell lysate or extract of said microorganism, or as immobilized esterase. The reaction products can be isolated from the reaction solution by chemical or physical separation processes known to the skilled worker. The esterase can be isolated from the reaction mixture by membrane filtration.

It is possible to immobilize the esterase with the aid of polyacrylamide, alginic acid or carrageenans. It is also possible to bind the esterase covalently or by adsorption to suitable carriers by means of known methods. The esterase is preferably immobilized by lyophilization on kieselguhr or by ammonium sulfate precipitation.

EXPERIMENTAL SECTION

Unless stated otherwise, the cloning steps carried out within the scope of the present invention, for example restriction cleavages, agarose gel electrophoresis, purification of DNA fragments, transfer of nucleic acids to nitrocellulose and nylon membranes, linking of DNA fragments, transformation of microorganisms, culturing of microorganisms, propagation of phages and sequence analysis of recombinant DNA, may be carried out as described in Sambrook et al. (1989), loc. cit.

Example 1

Selection of an Esterase-Expressing *Pseudomonas glumae* Mutant

Starting point of the screening was the lipase-producing strain *Pseudomonas (Burkholderia) glumae* LU8093. The lipase produced by said strain makes it possible to carry out a number of interesting reactions (Balkenhohl, F. et al., J. prakt. Chem. 339, (1997), 381-384). Lactic esters, methylbutyric esters and phenylacetic esters, however, are not substrates for the lipase and cannot be hydrolyzed by said strain in any other way either.

The hydrolysis products are, however, usable as carbon source. Therefore, mutants of LU8093 were sought which are able to hydrolyze said esters and to grow using the hydrolysis products as carbon source. Mutants with novel esterase activity should therefore reveal themselves by growing on said esters.

Selection Conditions:

LU8093 was cultured on medium for 16 h and harvested by centrifugation. The cells were washed twice with saline. $10^6$ cells were plated out onto minimal medium plates comprising 0.5 or 1.0 g/l ethyl phenylacetate as the sole carbon source. Initially, however, there was no growth. Only after 4 to 6 days were single colonies recognizable. Their number increased further over the following days.

From the esterase-positive mutants obtained in this way, the mutant LU2023 was selected. Surprisingly, the novel esterase activity was also suitable for selective hydrolysis of small organic molecules. As an example, selective hydrolysis was shown for butynol ester.

Example 2

Fermentation of *Pseudomonas glumae* LU2023

To obtain the esterase, *Pseudomonas glumae* LU2023 was cultured on a 14-1 scale and the active biomass was harvested.

In the laboratory, *Pseudomonas glumae* LU2023 was streaked onto agar plates with M12 mineral salt medium and 1 g/l EPA and incubated at 28° C. for 36 to 48 hours. The plates were then stored at 4° C. for four weeks.

Fermentation of the strain was carried out in an Infors xxy 14 l fermenter. For the preculture, 250 ml of medium were inoculated with 2 to 3 Pt loops and incubated at 200 rpm and 28° C. for 24 hours. The main culture was carried out under the following conditions:
Temperature 28° C.
Air feed 7 l/min
Stirring 600 rpm
Fermentation run time about 24 h
Built-in pH and $pO_2$ measurements
Medium for Preculture and Main Culture
15 g/l Springer yeast autolysate 65%
1.6 g/l magnesium sulfate×7 water
0.02 g/l calcium chloride×2 water
3.5 g/l potassium dihydrogen phosphate
3.5 g/l dipotassium hydrogen phosphate
5 g/l diammonium hydrogen phosphate
6 ml Pluriol P2000 antifoam The above ingredients were dissolved in deionized water and the solution was adjusted to pH 6.5 using 25% strength ammonia solution. 5 ml/l trace element solution and 2 g/l glucose were sterile-filtered separately.

After sterilizing and completing the medium, 0.5 g/l ethyl phenylacetate was introduced into the fermenter. Addition of Pluriol P2000 controlled the foam appearing during fermentation. Fermentation was stopped when the $pO_2$ in the fermenter increased again to above 85%. The fermenter contents were then centrifuged at below 15° C. and about 9000 to 10 000 g, and the clear effluent was discarded. The cell mass was frozen at −16° C.

Example 3

Purification of the Esterase from *Pseudomonas glumae* LU2023

*Pseudomonas glumae* (LU2023) cells (100 ml, wet weight: 50 g) were lysed in a glass bead mill (100 ml of glass beads, diameter: 0.5 mm) at 4° C. and 3000 rpm. After centrifugation (10 000 rpm, 30 min) and washing the glass beads, the supernatant (300 ml) was subjected to manganese chloride precipitation (pH 7 to 7.5; final concentration: 50 mM). After another centrifugation, the supernatant was adjusted to pH 8.0 and EDTA was added at a concentration of 50 mM. This volume was purified by Q-Sepharose (300 ml) chromatography. After applying the sample, the column was washed with 50 mM Tris/HCl. The fraction of interest was collected and concentrated by ultrafiltration (100 kDa). The butynol-hydrolyzing esterase was separated from a nonspecific esterase by molecular sieve chromatography (diameter: 5 cm, height: 90 cm; material: S-300). The active fraction obtained was cloudy and was again concentrated. The esterase was obviously membrane-bound. The membrane fraction was then first digested by a protease (trypsin, weight ratio: 1:50 to 1:100). This caused all proteins to disappear from the membrane fraction apart from a few bands in the SDS polyacrylamide gel electrophoresis. The activity was preserved. Said bands were separated from one another by native gel electrophoresis (0.04% SDS), and an activity assay identified the esterase in this native gel. Said esterase was eluted from the gel and then appeared as a clean band in a denaturing SDS polyacrylamide gel electrophoresis.

The protein purified in this way was transferred by blotting onto a PVDF membrane and sequenced, or, after trypsin cleavage, the peptides were separated by reversed phase HPLC and sequenced. Since the amino terminus of the protein was blocked, only tryptic peptides were obtained. The various amino acid sequences showed weak homologies to a muconate cycloisomerase, EC 5.5.1.1, from *Acinetobacter lwoffii* and *Pseudomonas putida*, and also to lactone esterase from *Pseudomonas fluorescens*. The peptide having the sequence AIDAIFAPEGV (SEQ ID NO: 24) showed homology to pectin esterases (EC 3.1.1.11).

The drawing in FIG. 1 depicts a sequence alignment of a partial amino acid sequence according to the invention sequence to a partial sequence of a lactone-specific esterase from *Pseudomonas fluorescens*.

Example 4

Immobilization of Esterase

Various methods were employed for the immobilization.
1. The esterase was substantially inactivated by precipitation with acetone in the presence of kieselguhr. 25 mg of protein were mixed with 3.5 g of kieselguhr (Merck), and 1.4 l of acetone (−20° C.) were added for 10 minutes. The loaded support was then removed via a G3 glass suction filter, the filter residue was washed with cold acetone and dried.
2. The esterase does not bind to Accurel (Akzo).
3. It was possible to immobilize the esterase (2.3 units/g, EPA assay) on kieselguhr by lyophilization. For this, the enzyme solution was mixed with kieselguhr and frozen at −80° C. Subsequently, the solid substance was dried by lyophilization.
4. The esterase (454 milliunits/g, EPA assay) was immobilized by ammonium sulfate precipitation. For this, the enzyme was precipitated at 80% saturation of ammonium sulfate in the presence of kieselguhr.

Example 5

Racemate Resolution using the Esterase from *Pseudomonas glumae* LU2023

Procedure (Standard Approach)
100 units of esterase were reacted with 20 mmol of butynol butyrate (1-methylprop-2-ynyl butyrate) in phosphate buffer (200 ml, 10 mM, pH 7.4) with stirring. The pH was continuously measured and kept at approx. pH 7.4 by adding sodium hydroxide solution. At the times indicated in table 1, samples were taken and extracted twice with methyl tert-butyl ether (MTBE), and the organic phase was analyzed by GC (Chiraldex GTA). The esterase could be removed from the reaction mixture by membrane filtration.

With its concentration increasing, the less preferred ester enantiomer was increasingly converted. After about 45 minutes, this caused a drop in the ee of S-butynol in the reaction mixture. The ee of the product reached its maximum at 84% (83-97.9%) after approx. 30 to 40 minutes. The ee of the substrate increased to over 99% over the course of 90 minutes. The ee (enantiomer excess) is defined as the amount of the preferably converted enantiomer in percent minus the amount of the less preferably converted enantiomer in percent. In most cases, this corresponds to the optical purity. The drop in pH was linear up to 30 minutes. From approx. 100 minutes onward, the pH change was negligible.

After the extraction, the residual esterase activity in the aqueous phase was still approx. 50%.

TABLE 1

| Time | ee of product (S)-butynol | ee of substrate (R)-butynol ester | Ester conversion in % (corr.) |
|---|---|---|---|
| 0 min | Nd | 5.20 | nd |
| 7 min | Nd | 10.20 | nd |
| 13 min | 75.50 | 20.40 | 12 |
| 20 min | 81.80 | 29.10 | 16 |
| 26 min | 83.90 | 42.00 | 22 |
| 32 min | 84.60 | 53.70 | 27 |
| 45 min | 84.00 | 78.80 | 36 |
| 70 min | 70.80 | 97.10 | 47 |
| 90 min | 69.60 | 99.10 | 52 |
| 121 min | 63.10 | 99.40 | 56 |
| 150 min | 52.00 | 99.50 | 67 |

Table 1 shows the time-dependent enantiomer excess on conversion of butynol butyrate by the esterase. According to the R/S convention by Cahn, Prelog and Ingold, R and S configurations define the two enantiomers of a chiral molecule. The conversion is the proportion of converted ester in the reaction mixture.

Example 6

Dependence of the Esterase Specificity on Size and Hydrophobicity/Charge of the Acid Moiety of the Ester Standard Approach
100 units of esterase were reacted with 20 mmol of butynol ester in phosphate buffer (200 ml, 10 mM, pH 7.4) with stirring. The pH was continuously measured and kept at pH 7.0 by continuous titration. Samples taken were extracted twice with methyl tert-butyl ether (MTBE), and the organic phase was analyzed by GC (Chiraldex GTA).
Result
The quality of racemate resolution and the reaction rate depended on size and hydrophobicity of the acid moiety. The best substrates for butynol esterase were butynol butyrate and butynol methylbutyrate. Lipases are inactive with these substrates. This is also true for long-chain esters such as butynyl n-decanoate.

TABLE 2

| Acid component | ee [%] | Conversion [%] | E |
|---|---|---|---|
| Acetate | 73 (S) | 48 | 12 |
| Butyrate | 95 (S) | 36 | 67 |
| Pentenoate | 74 (S) | 47 | 13 |

TABLE 2-continued

| Acid component | ee [%] | Conversion [%] | E |
|---|---|---|---|
| Hexanoate | 66 (S) | 44 | 8 |
| Octanoate | 64 (S) | 43 | 8 |
| 2-Ethylhexanoate | no conversion | | |
| Phenylacetate | 51 (S) | 12 | 3 |
| 3-Phenylpropionate | 73 (S) | 44 | 11 |
| 3-Cyclohexylpropionate | 22 (S) | 18 | 2 |

Table 2 shows the dependence of the enantiomer excess for the conversion of esters by the esterase on the acid moiety of the converted ester.

Example 7

Transesterification in Organic Medium using the Esterase 10 mmol of rac-butynol and 5 mmol of vinyl butyrate were dissolved in 50 ml of methyl tert-butyl ether (MTBE) and mixed with 9 units of esterase (3.3 g) supported on kieselguhr, and the mixture was shaken at room temperature for 24 h. After filtration, the solvent was removed and the product mixture was characterized by GC.

At 47% conversion, (R)-butynol (18% ee) and the butyrate of (S)-butynol (45% ee) remained.

In methyl isobutyl ketone, (R)-butynol with 16% ee and the butyrate of (S)-butynol with 52% ee were obtained at 43% conversion.

Table 3 shows the dependence of the enantiomer excess for the conversion of esters by the esterase on the acid moiety of the converted ester.

TABLE 3

| Mixture No. | Substrate | pH | Temp [° C.] | Buffer system sol. [mmol/l] | Additives | ee[1] |
|---|---|---|---|---|---|---|
| 8 | Butynyl n-decanoate | 7.0 | RT | Phosphate 10 | none | 54.37 |
| 14 | Butynyl n-pentanoate | 7.0 | RT | Phosphate 10 | none | 80.40 |
| 15 | Butynyl 2-ethylhexanoate | 7.0 | RT | Phosphate 10 | none | 81.77 |
| 16 | Butynyl butyrate | 7.0 | RT | Phosphate 10 | none | 83.90 |
| 17 | Butynyl butyrate | 7.0 | RT | Phosphate 10 | 0.5% Triton | 80.83 |
| 18 | Butynyl n-hexanoate | 7.0 | RT | Phosphate 10 | 0.5% Triton | 78.63 |
| 19 | Butynyl n-octanoate | 7.0 | RT | Phosphate 10 | 0.5% Triton | 74.70 |
| 20 | Butynyl butyrate | 7.0 | RT | Phosphate 10 | 10% n-Propanol | 87.47 |
| 21 | Butynyl butyrate | 7.0 | RT | Phosphate 10 | 1M NaCl | 85.70 |
| 23 | Butynyl n-pentanoate | 7.0 | RT | Phosphate 10 | 0.5% Triton | 84.40 |
| 24 | Butynyl butyrate | 6.0 | RT | Phosphate 10 | none | 85.37 |
| 25 | Butynyl butyrate | 8.0 | RT | Tris 10 | none | 85.33 |
| 26 | Butynyl butyrate | 7.0 | 10 | Phosphate 10 | none | 85.90 |
| 27 | Butynyl butyrate | 7.0 | 37 | Phosphate 10 | none | 75.67 |
| 28 | Butynyl 3-methylbutyrate | 7.0 | RT | Phosphate 10 | none | 90.50 |
| 29 | Butynyl methoxyacetate | 7.0 | RT | Phosphate 10 | none | 76.33 |
| 31 | Butynyl butyrate | 7.0 | RT | Phosphate 10 | none | 85.00 |
| 32 | Butynyl butyrate | 7.0 | RT | Phosphate 10 | 2-phase system | 84.93 |
| 33 | Butynyl 3-methylbutyrate | 7.0 | RT | Phosphate 10 | 2-phase system | 92.70 |
| 34 | Butynyl 2-methylpropionate | 7.0 | RT | Phosphate 10 | none | 89.17 |
| 35 | Butynyl 2-butenoate | 7.0 | RT | Phosphate 10 | none | 76.03 |
| 36 | Butynyl 3-chloropropionate | 7.0 | RT | Phosphate 10 | none | 71.13 |
| 40 | Butynyl 2-methylpentanoate | 7.0 | RT | Phosphate 10 | none | 85.93 |

[1]Averages of the 3 best values for ee of S-butynol

Example 8

Preparation of a Gene Library of Strain LU2023 and Cloning of LU2898 a) Obtaining Chromosomal DNA:

LU2023 (cf. examples 1 and 2 above) was grown in 100 ml of FP medium (Becton Dickinson GmbH) at 28° C. and 180 rpm for 24 h. The cells were harvested by means of centrifugation (2000 rpm/5 min), resuspended in 5 ml of lysis buffer 1 (0.41 M sucrose, 0.01 M $MgSO_4 \cdot 7H_2O$, 50 ml/L M12 medium (10× conc.), 10 mL 10% $KH_2PO_4$ pH 6.7, 2.5 mg/ml lysosyme [add shortly before use]) and incubated at 37° C. for approx. 4 h. After centrifugation (2000 rpm/20 min), the resulting protoplasts are washed in 5 ml of lysis buffer 1 without lysosyme (2000 rpm/20 min) and resuspended in 10 mM TRIS-HCl pH 8.0.

After another washing with 10 mM TRIS-HCl pH 8.0 (3000 rpm/5 min), the pellet was resuspended in 4 ml of TE buffer (10 mM TRIS-HCl, 1 mM EDTA, pH 8) and mixed with 0.5 ml each of SDS (10% w/v) and NaCl (5M). This was followed by adding 100 µl of proteinase K solution (200 µg/ml) and incubation at 37° C. for 16 hours. Subsequently, TE buffer was added to the solution to a final volume of 10 ml. This solution was admixed 1:1 with phenol. After centrifugation (4000 rpm/5 min), the upper phase was removed and mixed with a mixture of phenol, chloroform and isoamyl alcohol (12:12:1). The upper phase was removed and mixed with one volume of chloroform isoamyl alcohol (24:1). This procedure was repeated until the upper phase was clear.

DNA was precipitated from the upper phase by adding 2 volumes of ethanol and 1/50 volumes of $CH_3COONa$ (3M) at −20° C. (duration: approx. 30 min) and pelleted by centrifugation (12 000 rpm, 30 min, 4° C.) and resuspended in TE buffer. RNase (1 ml of a 20 µg/ml solution) hydrolyzes RNA at 37° C. within 1 h. The solution is then dialyzed against TE buffer at 4° C. three times for 1 hour each. The DNA is precipitated in aliquots of 0.4 ml each by adding ethanol (2 volumes plus 1/3 volume of LiCl, 2M) and incubation at −20° C. for 30 minutes. Centrifugation (15 000 rpm, 30 min, 4° C.) pelleted the DNA which was then dried. The DNA of a 0.4 ml aliquot was resuspended in 0.5 ml TE buffer.

b) Restriction of DNA and Cloning

1 µg of chromosomal DNA was digested with 120 U PstI at 37° C. for 180 min. 0.4 µg of pUC19 (e.g. New England Biolabs) was restricted with 160 U of PstI (1 h at 37° C.) and subsequently dephosphorylated with alkaline phosphatase (1 h at 37° C. plus inactivation at 65° C. for 15 minutes). The DNA fragments were ligated (2 h at room temperature) using the Rapid Ligation Kit (Roche). The ligation mixtures were transformed into transformation-competent *Escherichia coli* (Stratagene) according to the manufacturer's information. The cells were streaked out onto IPTG/X-Gal FP plates (FP medium containing 100 µg/ml ampicillin) and incubated at 37° C. for 16 hours. White colonies were streaked out onto fresh FP plates containing ampicillin.

c) Gene Library Screening

The colonies were transferred to Whatman filter paper using a sterile velvet cushion. The filters were placed in 2.5 ml of assay solution (10 mM TRIS*HCl, pH 7.5, 0.01% bromocresol purple, 0.1% racemic ester [rac-methyl lactate (MEE) or rac-ethyl methylbutyrate or rac-ethyl phenylacetate]). Colonies whose cells have esterase activity change color from blue to yellow within 5 minutes. Among the 2900 colonies assayed there was one which caused a strong color change. This strain was referred to as LU2898. FIG. 2 depicts a diagrammatic representation of the cloning strategy of LU2898.

Example 9

Sequence Analysis of Recombinant DNA of LU2898

The plasmid from LU2898 has a 7.7 kb insertion. The plasmid harboring the butynol esterase gene *E. coli* LU2898 was completely sequenced. A first search in DNA databases produced an open reading frame (positions 1394 to 2923), with the insert having a homology to hydrolytic enzymes.

The ERGO database (Integrated Genomics, Inc. ©1999-2004, Chicago, USA) was searched with the DNA sequence of LU2898 butynol esterase. Only the region from 1384 to 2397 by of the butynol esterase gene was found to be homologous to known hydrolases.

The region from 1384 to 2397 by is obviously the DNA of the desired butynol esterase. Another good indication is the GXSXG motif which is typical for serinecarboxyl esterases and which is located in amino acid positions 127-131 in the LU2023 butynol esterase.

The good agreement between the LU2898 butynol esterase gene and the *B. cepacia* hydrolase ends from about position 2400. Further down the reading frame, there is a very distinct homology to the 3' ends of NADP reductases.

These results are illustrated by attached FIG. 3. FIG. 3 is a summary of the ERGO analyses. The abrupt transition of homologies in the LU2898 butynol esterase coincides with a PstI cleavage site. Cleavage sites for the PstI restriction enzyme were not expected for the cloning strategy chosen. This enzyme was used for completely cleaving LU2023 chromosomal DNA for preparing the plasmid library. After complete hydrolysis, internal recognition sites for PstI should no longer be present. The finding of PstI cleavage sites in the LU2898 plasmid can be explained by the fact that different gene fragments produced by said PstI restriction were connected to one another during plasmid construction and eventually ligated into the PstI cleavage site of pUC19, meaning that the reading frame assigned to butynol esterase possibly represents only part of the actual gene from *Ps. glumae* LU2023. The butynol esterase gene has been disrupted at the PstI site and subsequently connected to a fragment of an NADP reductase gene.

This hypothesis is supported by protein sequencing data. *Ps. glumae* LU2023 butynol esterase has been purified. The amino acid sequence of the protein was determined by Edman degradation. The complete sequence is known except a few N- and C-terminal amino acids. It corresponds to the amino acid sequence from the first part of butynol esterase, derived from the DNA data of LU2898. The experimentally determined molecular weight of butynol esterase of 41.3 kDa is markedly lower than the value derived from the DNA sequence of the recombinant LU2898 butynol esterase gene. According to the DNA sequence data, butynol esterase should have a molecular weight of 55 kDa.

Evidence was found with the aid of the database analysis that the butynol esterase has not been cloned in its full length. The plasmid from LU2898 does not comprise the 3' end of the butynol esterase gene.

Example 10

Finding of Clone LU11147 Comprising a Truncated 335AA Butynol Esterase Mutant

The sequence data of the plasmid from LU2898 were utilized in order to design the following PCR primers.

```
Breu0811:
    HindIII
GGCGAGAAGCTTAGAAATCATGATCGTCCA    (SEQ ID NO: 20)

Breu0812:
    XbaI
GGATCCTCTAGAGTCTCACTGCAGCGGGCC    (SEQ ID NO: 21)
```

These oligonucleotides were used to amplify by means of PCR the DNA from LU2898, which has the above-described homology to esterase.

PCR Conditions:

| | |
|---|---|
| 5 µl | of 10*Taq polymerase buffer |
| 125 ng | of primer Breu0811 |
| 125 ng | of primer Breu0812 |
| 2 µl | of dNTP (10 mM) |
| 50 ng | of plasmid DNA from LU11147 |
| 2.5 µl | of DMSO |
| ad 50 µ | of H$_2$O |
| hot start with: 0.5 U | of Taq-DNA polymerase (Roche Diagnostics) |

PCR Temperature Program:

| | |
|---|---|
| 5 min, 95° C., | |
| 45 s, 55° C., | |
| 3 min, 72° C., | } (30 cycles) |
| 30 s, 95° C., | |
| 45 s, 55° C., | |
| 10 min, 72° C., | |
| ∞, 4° C. | |

After restriction with HindIII and XbaI, the PCR product is ligated into an appropriately prepared pUC19 (e.g. New England Biolabs).

The plasmid vector prepared in this way was then used for transforming *E. coli* XL1 blue. The ligation mixtures were transformed into transformation-competent *Escherichia coli* (Stratagene) according to the manufacturer's information. The cells were streaked out onto IPTG/X-Gal FP plates (FP medium containing 100 µg/ml ampicillin) and incubated at 37° C. for 16 hours. Plasmid DNA was prepared from the transformants (Birnboim et al., Nucleic Acids Research, 1979, 7, 1513) and checked for successful insertion of the PCR product by means of control restriction with HindIII and XbaI.

Example 11

Expression of the Truncated 335 AA Butynol Esterase

The esterase gene was subsequently cloned into the vector pDHE1650 (described in WO-A-2004/050877), using the NdeI and HindIII cleavage sites.

To this end, the esterase gene was first amplified using the following forward and reverse primers:

```
Breu1499   TATACATATGATCGTCCAACTGATCGCCATCGTG,

Breu1500   ATTTAAGCTTTTACTGCAGCGCGCCGGCCTGCGTGACCTC
``` followed by restriction digest using NdeI and HindIII. The insert was ligated into the pDHE1650 vector which previously had been predigested with the same restriction enzymes (NdeI and HindIII). In the same way, the place holder gene present in pDHE1650 was replaced with the esterase gene of the invention. Two transformants were isolated and the plasmids were extracted by DNA precipitation in a manner known per se. Said plasmids were referred to as pDHE1650-Est2 and pDHE1615-Est4.

For protein expression, the plasmid carrying the esterase gene was transformed into *Escherichia coli* TG1 (DSMZ No. 6056), using the TSS method ([Chung C T, Niemela S L and Miller R H, 1989. One-step preparation of competent *Escherichia coli*: Transformation and Storage of Bacterial Cells in the Same Solution. Proc. Natl. Acad. Sci. U.S.A. 86: 2172-2175). A single colony was isolated and propagated in 5 ml of LB/Amp/Tet/Spec/Cm medium (=LB medium according to Sambrook, J., Fritsch, E. F. and Maniatis, T. Molecular cloning: A Laboratory Manual. 2nd Ed., Cold Spring Harbor Laboratory, Cold Spring Harbor Laboratory Press, Cold Spring Harbor, N.Y., 1989 plus 100 µg/ml ampicillin, 10 µg/ml tetracycline, 100 µg/ml spectinomycin and 20 µg/ml chloramphenicol) at 37° C. and 250 rpm overnight. 100 ml of LB/Amp/Tet/Spec/Cm medium supplemented with 10 ml/l trace element solution were inoculated with 500 µl of the overnight culture and propagated at 37° C. and 200 rpm. (The trace element solution is composed as follows: $FeSO_4*H_2O$ 200 mg/l, $ZnSO_4*7H_2O$ 10 mg/l, $MnCl_2*4H_2O$ 3 mg/l, $H_3BO_3$ 30 mg/l, $CoCl_2*6H_2O$ 20 mg/l, $CuCl_2*6H_2O$ 1 mg/l, $NiCl_2*6H_2O$ 2 mg/l, $Na_2MoO_4*2H_2O$ 3 mg/l, Titriplex III 500 mg/l). Protein expression was induced with 1 mM L-Rhamnose once $OD_{600}$ had reached a value of from 0.5 to 0.6. The temperature was reduced to 30° C., while the rate of rotation was kept at 200 rpm. The culture was cultured overnight. Subsequently, the cells were centrifuged (15 min, 4° C., 3220 g) and the cell pellet was stored at −20° C. overnight.

The cells were disrupted by resuspending the cell pellet (of 50 ml of TB culture) in sodium phosphate buffer (25 mM, ionic strength 154 mM, pH 7.5). The cells were disrupted by homogenization (1500 bar, 2 passages). Cell fragments were removed by centrifugation (30 min, 4° C., 20 817 g). The supernatant was applied to a Protein 200 Plus Labchip and analyzed for protein using the Agilent 2100 Bioanalyzer. The removed cell fragments were resuspended in 8 M urea, followed by centrifugation (30 min, 4° C., 20 817 g) in order to remove undissolved particles. The clear supernatant (membrane fraction) was applied to a Protein 200 Plus-Labchip and analyzed for protein using the Agilent 2100 Bioanalyzer.

Example 12

Preparation of Butynol Esterase (335AA) Mutants a) Materials

All chemicals used were suitable for analytical purposes or had a higher quality and were purchased from Sigma-Aldrich Chemie, Taufkirchen, Germany, Applichem (Darmstadt, Germany) and Carl Roth (Karlsruhe, Germany).

A thermocycle (Mastercycler gradient, Eppendorf, Hamburg, Germany) and thin-wall PCR tubes (Multi-Ultra tubes; 0.2 ml; Carl Roth) were used in all PCR experiments. The PCR volume was in each case 50 µl; larger volumes were prepared by way of multiple 50 µl PCR mixtures. The amount of DNA used was quantified using a NanoDrop photometer (NanoDrop Technologies, Wilmington, Del.).

b) Cloning of Butynol Esterase Gene into pASK-IBA7 Vector:

The pASK-IBA7 vector (IBA GmbH, Göttingen, Germany) (SEQ ID NO: 19, plasmid for protein expression with N-terminal Strep-tag) was amplified using the following primers:

```
Forward primer
                                     (SEQ ID NO: 9)
5'-TTTTTGCCCTCGTTATCTAGATTT-3'

Reverse primer
                                    (SEQ ID NO: 10)
5'-CCGGAATTCCGGTATCTAACTAAGCTTGACCTG-3'
```

The 50 µl PCR mixture (95° C. 3 min; 1 cycle//95° C. 30 s, 56.2° C. 45 s, 72° C. 7 min; 30 cycles//72° C. 10 min; 1 cycle) comprised: 20 µmol of forward primer, 20 µmol of reverse primer, 0.2 mM of each dNTP (Roche Diagnostics GmbH, Mannheim, Germany), 150 ng of pASK-IBA7 plasmid and 2.5 U of Pfu DNA polymerase (Fermentas GmbH, St. Leon-Rot, Germany). The product was purified by gel, using the QIAquick gel extraction kit (Qiagen, Hilden, Germany) and again amplified under conditions identical to those above. After gel purification (QIAquick gel extraction kit, Qiagen), 2 µg of the DNA product were digested with 40 U of EcoRI (New England Biolabs GmbH, Frankfurt, Germany) in a 100 µl reaction mixture at 37° C. for 4 hours. The digested product was PCR-purified using the QIAquick PCR purification kit (Qiagen).

The butynol esterase gene was amplified using the following primers:

```
Forward primer
                                    (SEQ ID NO: 11)
5'-[Phos]GACCATGATTACGCCAAGCTTGC-3'

Reverse primer
                                    (SEQ ID NO: 12)
5'-CCGGAATTCCGGTCACTGCAGCGCGCCGGCCTG-3'.
```

The 50 µl PCR mixture (95° C. 2 min; 1 cycle//95° C. 30 s, 59° C. 45 s, 72° C. 3 min; 30 cycles//172° C. 10 min; 1 cycle) comprised: 20 µmol of forward primer, 20 µmol of reverse primer, 0.2 mM of each dNTP (Roche Diagnostics GmbH); 150 ng of plasmid LU11147 (pUC19 vector, carrying the butynol esterase gene), 0.02% DMSO and 2.5 U of Pfu DNA polymerase (Fermentas). After gel purification (QIAquick gel extraction kit, Qiagen), 2 µg of the DNA product were digested with 40 U of EcoRI (New England Biolabs GmbH, Frankfurt, Germany) in a 100 µl reaction mixture at 37° C. for 4 hours.

The digested product was PCR-purified using the QIAquik PCR purification kit (Qiagen).

The butynol esterase gene was ligated into the vector using blunt and EcoRI cleavage sites. The reaction mixture (20 μl) comprised: 20 ng of vector, 120 ng of insert and 2 U of T4 DNA ligase (Roche Diagnostics GmbH). The reaction mixture was first incubated at room temperature for 1 hour, followed by overnight incubation in a refrigerator. The resulting plasmid was referred to as pASK-IBA7 esterase.

c) Preparation of the First Butynol Esterase Mutant Library:

The butynol esterase gene was first amplified by means of error-prone PCR (95° C. 2 min; 1 cycle//95° C. 30 s, 59° C. 45 s, 72° C. 3 min; 40 cycles//72° C. 10 min). The following primers were used:

```
Forward primer:
5'-CGACAAAAATCTAGATAACGAGGGCAA-3'   (SEQ ID NO: 13)

Reverse primer:
5'-TTGACTTCACAGGTCAAGCTTAGTTAG-3'.  (SEQ ID NO: 14)
```

The reaction mixture (50 μl) comprised: 20 μmol of forward primer, 20 μmol of reverse primer, 0.2 mM of each dNTP (Roche Diagnostics GmbH), 100 ng of plasmid pASK-IBA7 esterase, 0.02% DMSO, 0.1 mM $MnCl_2$ and 2.5 U of Taq DNA polymerase (Qiagen). After gel purification (QIAquick Gel Extraction Kit; Qiagen), 4 μg of DNA were double-digested with 40 U of EcoRI (New England Biolabs GmbH) and 30 U of XbaI (New England Biolabs GmbH). The product was PCR-purified (QIAquick PCR-Purification Kit; Qiagen) before being ligated into the EcoRI- and XbaI-pre-digested pASK-IBA7 plasmid. The mutant library was transformed into *E. coli* XL2Blue (Stratagene, Amsterdam) using the TSS method [Chung C T, Niemela S L and Miller R H, 1989. One-step preparation of competent *Escherichia coli*: Transformation and Storage of Bacterial Cells in the Same Solution. Proc. Natl. Acad. Sci. U.S.A. 86: 2172-2175.].

d) Expression of the Butynol Esterase Mutant Library:

Colonies on $LB_{amp}$ plates (=LB medium according to Sambrook, J., Fritsch, E. F. and Maniatis, T. Molecular Cloning: A Laboratory Manual. 2nd Ed., Cold Spring Harbor Laboratory, Cold Spring Harbor Laboratory Press, Cold Spring Harbor, N.Y., 1989 plus 10 g/l agar and 100 μg/m ampicillin) were picked using toothpicks and transferred to microtiter plates with 96 wells containing 150 μl of $LB_{amp}$ medium. After culturing in a microplate shaker (Multitron II; Infors GmbH, Einsbach, Germany; 37° C., 900 rpm and 70% humidity), ~5 μl of each culture were transferred using system Duetz (Kühner, Birsfelden, Switzerland) to plates with 2 ml wells containing 550 μl of TB medium with 100 μg ml ampicillin (Becton Dickinson GmbH). The clones were cultured in a Multitron II shaker (Infors GmbH; 30° C. and 500 rpm and 70% humidity) for 8 hours. Protein expression was induced by adding 50 μl TB comprising 2.4 μg/ml anhydrotetracycline (IBA GmbH) to each well. The clones were cultured for another 6 hours in a Multitron II shaker (Infors GmbH; 30° C. and 500 rpm) for 8 hours.

e) pH Indicator Assay (96-Well Format):

A 50 μl TB culture from each well was transferred to 96-well assay plates using a Multimek 96-channel automatic pipetter (Beckman Coulter, Krefeld, Germany). The hydrolytic reaction was started by adding 100 μl of substrate solution (25 mM $NaH_2PO_4$ buffer, pH 7.5, ionic strength 154 mM, adjusted with NaCl, comprising 0.05% Triton X-100, 7.5 μg/ml fluorescein-sodium and 285 mM but-3-yn-2-yl butyrate) to each well of the assay plate, using a Multimek 96 (Beckman Coulter). The substrate solution was agitated vigorously for 5 min prior to use. The kinetics of reduction of the fluorescence signal (extinction 485 nm, emission 520 nm) was observed using Tecan Safire (Tecan GmbH, Crailsheim, Germany) for 10 min. The activity was determined from the initial slope. After the screening of 930 clones, clone 8H1 was identified as an improved mutant.

f) Second Butynol Esterase Mutant Library:

A second butynol esterase mutant library was generated under exactly the same conditions as described above, except that 8H1 was used as parental gene. The library was expressed and screened as above. After a screening of 1116 clones, clone 8C9 was identified as improved mutant.

g) Saturation Mutagenesis in Amino Acid Positions 190 and 263:

A saturation mutagenesis of amino acid positions 190 and 263 was carried out using the following modified QuikChange protocols (Stratagene). The following mutagenesis primers were used for amino acid position 190:

```
                                    (SEQ ID NO: 15)
5'-GGCATCCCGATCATGNNNCTGCAAAGCCGCAAG-3'

(SEQ ID NO: 16)
5'-CTTGCGGCTTTGCAGNNNCATGATCGGGATGCC-3'
```

The following mutagenesis primers were used for amino acid position 263:

```
                                    (SEQ ID NO: 17)
5'-GGGCGCCAGGACGCGNNNCTCGATTTCCACAAG-3'

(SEQ ID NO: 18)
5'-CTTGTGGAAATCGAGNNNCGCGTCCTGGCGCCC-3'
```

The 50 μl PCR mixture (95° C. 30 s; 1 cycle//95° C. 30 s, 55° C. 1 min, 68° C. 4 min 45 s; 18 cycles) comprised a mixture of 20 μmol of each primer, 0.2 mM of each dNTP (Roche Diagnostics GmbH), 50 ng of plasmid 8C9 (starting DNA) and 2.5 U of Pfu Turbo DNA polymerase (Stratagene). The PCR was followed by digesting methylated and hemi-methylated parental DNA with 40 U of DpnI (New England Biolabs GmbH) at 37° C. for 2 to 3 hours. The products were PCR-purified (QIAquick PCR-Purification Kit; Qiagen) and then transformed into *E. coli* XL2Blue (Stratagene) using the TSS method [Chung C T, loc. cit].

The two libraries were expressed and screened in a manner identical to that described above. After a screening of 186 clones for each library, two clones were identified as improved mutants. These were referred to as Est190-1 B2 and Est263-2D6.

h) Protein Expression in Shaker Flasks

Overnight cultures were grown in 5 ml of $LB_{amp}$ medium using a Multitron-II shaker (Infors GmbH; 37° C., 250 rpm) by picking a freshly transformed colony. 100 ml of $TB_{amp}$ medium were inoculated with 800 μl of said overnight culture and cultured in a Multitron-II shaker (Infors GmbH; 37° C., 200 rpm). Once $OD_{600}$ values of from 0.5 to 0.6 had been reached, protein expression was induced by adding 25 μl of anhydrotetracycline (stock solution of 0.2 mg/ml in DMF). The culture was grown for another 12 hours (Multitron-II shaker, Infors GmbH; 30° C., 200 rpm). The cells were removed by centrifugation at 3220 g and 4° C. for 30 min and the wet cell mass was determined. The cell pellets were stored at −20° C. until further characterization.

i) Protein Characterization using pH Stat:

The hydrolytic activity of butynol esterase was measured using pH stat (716 DMS Titrino, Deutsche Metrohm GmbH & Co., Filderstadt, Germany).

The cell pellets were first resuspended in a suitable volume of sodium phosphate buffer (25 mM sodium dihydrogen phosphate buffer, pH 7.5, ionic strength: 154 mM, adjusted with NaCl) in order to obtain a cell concentration of 0.1 g of wet cell mass/ml. 20 ml of substrate solution comprising sodium phosphate buffer (25 mM NaH$_2$PO$_4$ buffer, pH 7.5, ionic strength: 154 mM, adjusted with NaCl), 0.05% Triton X-100 and 350 mM but-3-yn-2-yl butyrate were prepared. The substrate solution was agitated vigorously for 5 min prior to use.

The pH of the substrate solution (20 ml) was adjusted to pH 7.5 with 1N NaOH prior to starting the hydrolytic reaction. The reaction was started by adding 0.01 g of wet cell mass. A pH of 7.5 was maintained by titration with 0.1N NaOH during bioconversion. The hydrolytic activity was correlated to the rate of titration of NaOH (volume, added per unit time).

The results are depicted in attached FIG. 4. The enzymes and mutants listed in the following table were assayed. Information regarding the particular mutation in the amino acid sequence and nucleic acid sequence can likewise be found in said table.

| Clones | Amino acid position | | |
|---|---|---|---|
| | 16 | 190 | 263 |
| pASK-IBA7-Esterase | ctg (L) | att (I) | atc (I) |
| 8H1 | ccg (P) | act (T) | atc (I) |
| 8C9 | ccg (P) | act (T) | gtc (V) |
| Est190-1B2 | ccg (P) | cgc (R) | gtc (V) |
| Est 263-2D6 | ccg (P) | act (T) | gtt (V) |

What is claimed is:

1. An isolated mutant protein having esterase activity, wherein said isolated mutant protein consists of an amino acid sequence which is at least 95% identical to the amino acid sequence of SEQ ID NO: 8 and differs from the amino acid sequence of SEQ ID NO: 8 by a mutation in an amino acid position corresponding to any one of residues 12-20 and 185-195 of the amino acid sequence of SEQ ID NO: 8, wherein said isolated mutant protein cleaves the ester but-3-yn-2-yl butyrate, and wherein the isolated mutant protein has a calculated molecular weight of 38 to 34 kDa.

2. An isolated esterase mutant having esterase activity, wherein said isolated esterase mutant differs from the amino acid sequence of SEQ ID NO: 2 or 8 by a first mutation in any of amino acid positions corresponding to residues 12-20 of the amino acid sequence of SEQ ID NO: 2 or 8 and a second mutation in any of amino acid positions corresponding to residues 185-195 of the amino acid sequence of SEQ ID NO: 2 or 8, and wherein said isolated esterase mutant has at least 95% amino acid sequence identity to the amino acid sequence of SEQ ID NO: 2 or 8.

3. The isolated esterase mutant according to claim 2, wherein the first mutation is at the amino acid position corresponding to residue 16 of the amino acid sequence of SEQ ID NO: 2 or 8 and the second mutation is at the amino acid position corresponding to residue 190 of the amino acid sequence of SEQ ID NO: 2 or 8.

4. The isolated esterase mutant according to claim 3, wherein the first and/or second mutation is selected from the group consisting of Leu16Pro, Ile190Thr, and Ile190Arg.

5. The isolated mutant protein according to claim 1, wherein said isolated mutant protein catalyzes at least one of the following reactions:
   a) enantioselective hydrolysis of optically active esters of the formula I $$R^1\text{—COO—}R^2 \qquad (I),$$

in which
   $R^1$ is a straight-chain or branched, optionally mono- or polysubstituted $C_1$-$C_{10}$-alkyl, $C_2$-$C_{10}$-alkenyl, $C_2$-$C_{10}$-alkynyl, and $R^2$ is a straight-chain or branched, optionally mono- or polysubstituted $C_1$-$C_{10}$-alkenyl, $C_2$-$C_{10}$-alkynyl, $C_7$-$C_{15}$-aralkyl or a mono- or polynuclear, optionally mono- or polysubstituted aromatic radical,
   $R^1$ and/or $R^2$ comprise at least one asymmetric carbon; and
   b) enantioselective transesterification of an ester of the formula I with an optically active alcohol of the formula II $$R^2\text{—OH} \qquad (II),$$

in which $R^2$ is a straight-chain or branched, optionally mono- or polysubstituted. $C_1$-$C_{10}$-alkyl, $C_2$-$C_{10}$-alkenyl, $C_2$-$C_{10}$-alkynyl, $C_7$-$C_{15}$-aralkyl or a mono- or polynuclear, optionally mono- or polysubstituted aromatic radical and comprises at least one asymmetric carbon.

6. A process for enantioselective ester hydrolysis using the isolated mutant protein according to claim 1, which process comprises
   a) contacting said isolated mutant protein with a stereoisomer mixture of an optically active ester of the formula $R^1\text{—COO—}R^2$ (formula I) in a reaction medium to enantioselectively hydrolyze the stereoisomer mixture and produce optically active compounds; and
   b) obtaining the optically active compounds from the reaction medium,
   wherein $R^1$ is a straight-chain or branched, optionally mono- or polysubstituted $C_1$-$C_{10}$-alkyl, $C_2$-$C_{10}$-alkenyl, $C_2$-$C_{10}$-alkynyl, and $R^2$ is a straight-chain or branched, optionally mono- or polysubstituted $C_1$-$C_{10}$-alkyl, $C_2$-$C_{10}$-alkenyl, $C_2$-$C_{10}$-alkynyl, $C_7$-$C_{15}$-aralkyl or a mono- or polynuclear, optionally mono- or polysubstituted aromatic radical, and $R^1$ and/or $R^2$ comprise at least one asymmetric carbon.

7. A process for enantioselective transesterification, which comprises
   a) contacting a stereoisomer mixture of an optically active alcohol of the formula $R^2\text{—OH}$ (formula II) with an ester of the formula $R^1\text{—COO—}R^2$ (formula I) in the presence of the isolated mutant protein according to claim 1 in a reaction medium and obtaining the unreacted alcohol stereoisomer from the reaction medium; or
   b) contacting a stereoisomer mixture of an optically active ester of the formula I with an alcohol of the formula II in the presence of said isolated mutant protein in a reaction medium and
   obtaining a stereoisomer of the optically active alcohol from the reaction medium,
   wherein $R^1$ of formula I is a straight-chain or branched, optionally mono- or polysubstituted $C_1$-$C_{10}$-alkyl, $C_2$-$C_{10}$-alkenyl, $C_2$-$C_{10}$-alkynyl, and $R^2$ of formula I is a straight-chain or branched, optionally mono- or polysubstituted $C_1$-$C_{10}$-alkyl, $C_2$-$C_{10}$-alkenyl, $C_2$-$C_{10}$-alkynyl, $C_7$-$C_{15}$-aralkyl or a mono- or polynuclear, optionally mono- or polysubstituted aromatic radical, and $R^1$ and/or $R^2$ comprise at least one asymmetric carbon, and
   wherein $R^2$ of formula II is a straight-chain or branched, optionally mono- or polysubstituted $C_1$-$C_{10}$-alkyl, $C_2$-$C_{10}$-alkenyl, $C_2$-$C_{10}$-alkynyl, $C_7$-$C_{15}$-aralkyl or a mono- or polynuclear, optionally mono- or polysubstituted aromatic radical and comprises at least one asymmetric carbon.

8. The process according to claim 7, wherein the ester is a vinyl ester.

9. The process according to claim 6, wherein the reaction medium comprises an organic solvent.

10. The process according to claim 7, wherein the reaction medium comprises an organic solvent.

11. An isolated esterase mutant having esterase activity, wherein said isolated esterase mutant differs from the amino acid sequence of SEQ ID NO: 2 or 8 by a first mutation in any of amino acid positions corresponding to residues 12-20 of the amino acid sequence of SEQ ID NO: 2 or 8, a second mutation in any of amino acid positions corresponding to residues 185-195 of the amino acid sequence of SEQ ID NO: 2 or 8, and a third mutation in any of amino acid positions corresponding to residues 258-268 of the amino acid sequence of SEQ ID NO: 2 or 8, and wherein said isolated esterase mutant has at least 95% amino acid sequence identity to the amino acid sequence of SEQ ID NO: 2 or 8.

12. The isolated esterase mutant according to claim 11, wherein the third mutation is at the amino acid position corresponding to residue 263 of the amino acid sequence of SEQ ID NO: 2 or 8.

13. The isolated mutant protein according to claim 1, wherein the isolated mutant protein has a total length of 335 amino acids and consists of an amino acid sequence which is at least 95% identical to the amino acid sequence of SEQ ID NO: 8.

14. The isolated esterase mutant according to claim 11, wherein the first mutation is at the amino acid position corresponding to residue 16 of the amino acid sequence of SEQ ID NO: 2 or 8, the second mutation is at the amino acid position corresponding to residue 190 of the amino acid sequence of SEQ ID NO: 2 or 8, and the third mutation is at the amino acid position corresponding to residue 263 of SEQ ID NO: 2 or 8.

\* \* \* \* \*